(12) United States Patent
Brown et al.

(10) Patent No.: US 10,344,047 B2
(45) Date of Patent: *Jul. 9, 2019

(54) OLIGONUCLEOTIDE LIGATION

(75) Inventors: Tom Brown, Southampton (GB); Afaf Helmy El-Sagheer, Southampton (GB)

(73) Assignee: ATDBIO LTD., Southampton (GB)

( * ) Notice: Subject to any disclaimer, the term of this patent is extended or adjusted under 35 U.S.C. 154(b) by 688 days.

This patent is subject to a terminal disclaimer.

(21) Appl. No.: 13/409,929

(22) Filed: Mar. 1, 2012

(65) Prior Publication Data

US 2013/0231473 A1    Sep. 5, 2013

(51) Int. Cl.
*C07H 21/04* (2006.01)

(52) U.S. Cl.
CPC .................................. *C07H 21/04* (2013.01)

(58) Field of Classification Search
CPC ...................................................... C07H 21/04
See application file for complete search history.

(56) References Cited

U.S. PATENT DOCUMENTS 8,846,883 B2 *  9/2014  Brown et al. ................ 536/23.1

FOREIGN PATENT DOCUMENTS

WO   WO 2008/120016 A1   10/2008

OTHER PUBLICATIONS (R) Ning et al., "Visualizing Metabolically Labeled Glycoconjugates of Living Cells by Copper-Free and Fast Hiusgen Cycloadditions," Angew. Chem. Intl. Ed., 47(12), 2253-2255 (2008).*
El-Sagheer et al., "Biocompatible artificial DNA linker that is read through by DNA polymerases and is functional in *Escherichia coli*," PNAS, vol. 108, No. 28, pp. 11338-11343 (Jul. 12, 2011).
El-Sagheer et al., "New strategy for the synthesis of chemically modified RNA constructs exemplified by hairpin and hammerhead ribozymes," PNAS, vol. 107, No. 35, pp. 15329-15334 (Aug. 31, 2010).
El-Sagheer et al., "Synthesis and Polymerase Chain Reaction Amplification of DNA Strands Containing an Unnatural Triazole Linkage," J. Am. Chem. Soc., vol. 131, No. 11, pp. 3958-3964 (Mar. 26, 2009).
Kocalka et al., "Rapid and Efficient DNA Strand Cross-Linking by Click Chemistry," ChemBioChem, vol. 9, pp. 1280-1285 (2009).
Kumar et al., "Template-Directed Oligonucleotide Strand Ligation, Covalent Intramolecular DNA Circularization and Catenation Using Click Chemistry," J. Am. Chem. Soc., vol. 129, pp. 6859-6864 (2007).
Chen, Xiong et al, "Reverse transcription through a bulky triazole linkage in RNA: implications for RNA sequencing", *Chem. Commun.*, 2014, 50, 7597, Apr. 23, 2014, 4 pages.
Chelsea G. Gordon et al., "Reactivity of Biarylazacyclooctynones in Copper-Free Click Chemistry," *J. Am. Chem. Soc.* 2012, 134, 9199-9208, 10 pages.
Julian A. Codelli et al., "Second-Generation Difluorinated Cyclooctynes for Copper-Free Click Chemistry," J. Am. Chem. Soc. 2008, 130, 11486-11493, 8 pages.
Qui, Jieqiong et al., "Solid phase click ligation for the synthesis of very long oligonucleotide", *Chem. Commun.*, 2013, 49, 6959-6961, Jun. 21, 2013;•3 pages.
Shelbourne, Montserrat et al., "Fast copper-free click DNA ligation by the ring-strain promoted alkyne-azide cycloaddition reaction" (Chem. Commun., 2011, 47, 6257-6259, May 6, 2011; 3 pages.

* cited by examiner

*Primary Examiner* — Lawrence E Crane
(74) *Attorney, Agent, or Firm* — Patterson Thuente Pedersen, P.A.

(57) ABSTRACT

Embodiments are directed to methods for joining oligonucleotides. The methods include joining together one or more oligonucleotides by reacting an alkyne group linked to an oligonucleotide with an azide group linked to an oligonucleotide to form a triazole linkage. The alkyne group is a strained alkyne group. The methods can include ligating together ends of one or more oligonucleotides or cross-linking strands of an oligonucleotide duplex to form the triazole linkage. The methods described allow oligonucleotide strands to be ligated together without the need for a ligase enzyme. The methods can be useful for joining together single strands of DNA, cross-linking complementary strands, cyclizing single and double strands, labeling oligonucleotides with reporter groups, attaching DNA to surfaces, producing analogs of DNA with modified nucleobases and backbones, synthesizing large chemically modified RNA constructs, and creating biochemically active PCR templates.

31 Claims, 7 Drawing Sheets
Specification includes a Sequence Listing.

a. Crosslinking two complementary DNA or RNA strands
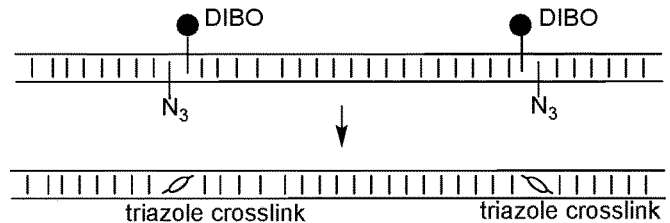
b. Ligating DNA or RNA strands (template-mediated)
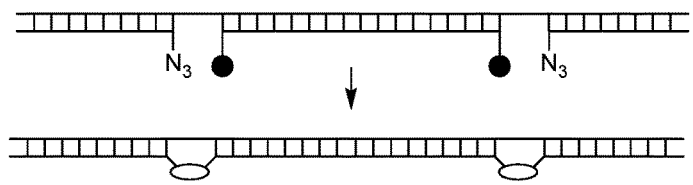
c. Chemical reaction: an example below
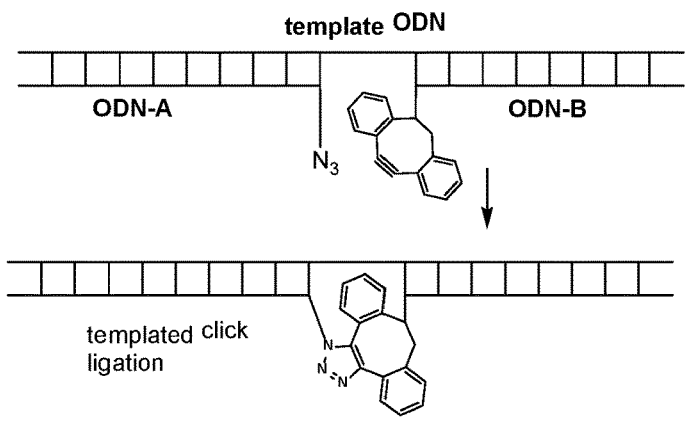
d. Use of methods a or b above to join together proteins, nanoparticles, magnetic beads etc
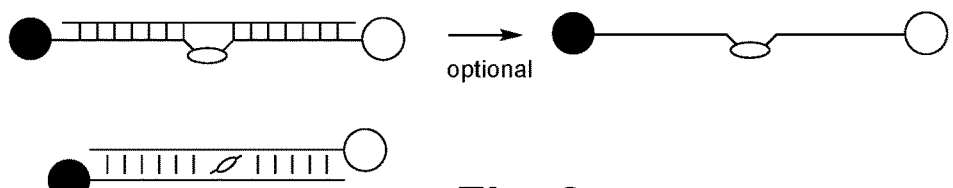
Fig. 2

DIBO monomers made and put into DNA

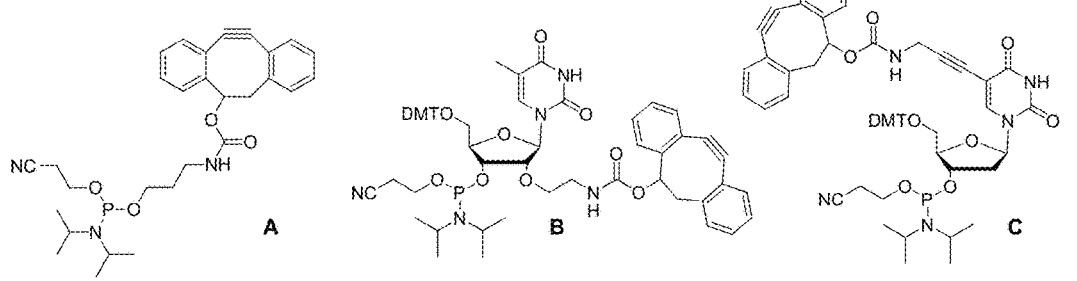

A — DIBO monomer for labelling oligonucleotides at 5'-position

B — 2'-DIBO dT monomer for labelling oligonucleotides internally (minor/major groove)

C — 5-DIBO propargyl dT monomer for labelling oligonucleotides internally (major groove)

precursors to azide monomers and azides put into DNA

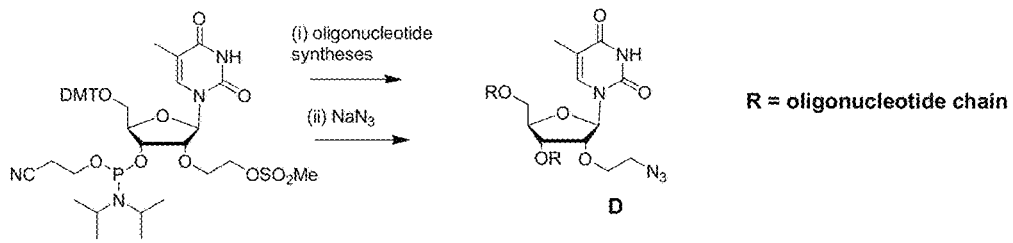

R = oligonucleotide chain

2'-ethoxymesyl-T monomer for labelling oligonucleotides internally (minor/major groove)

D — 2'-azidoethoxy-T incorporated in oligonucleotides internally via amino derivative (minor/major groove)

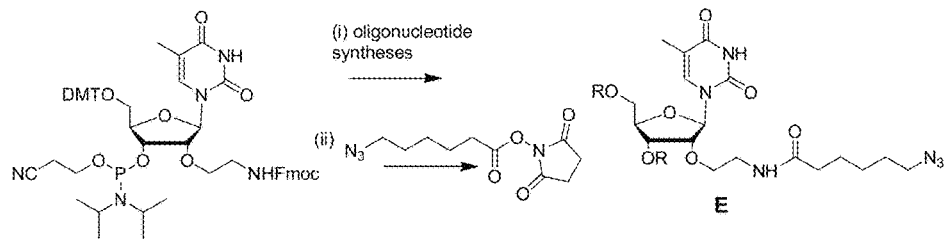

2'-aminoethoxy-T monomer for labelling oligonucleotides internally via amino derivative (minor/major groove)

E — 2'-azidoethoxy-T incorporated in oligonucleotides internally (minor/major groove)

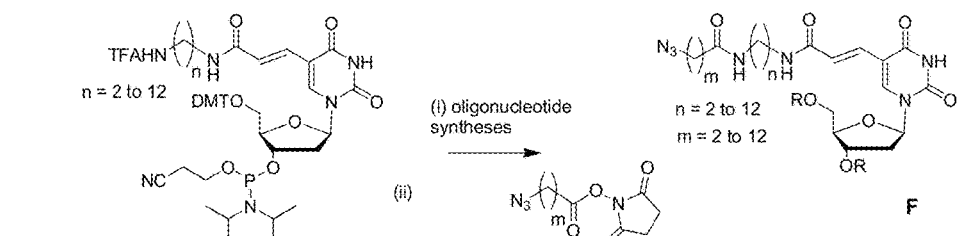

5-aminoalkyl dT monomer for labelling oligonucleotides internally (major groove)

F — 5-azidoalkyl dT in oligonucleotides internally (major groove)

*Fig. 6*

OLIGONUCLEOTIDE LIGATION

FIELD OF THE INVENTION

This invention relates to a method for joining oligonucleotides. In particular, it relates to a metal ion catalysis free, templated oligonucleotide joining method for ligating oligonucleotides end to end or cross-linking oligonucleotide strands. It also relates to use of a ring-strain promoted alkyne-azide [3+2] cycloaddition reaction, (a SPAAC reaction) between a strained alkyne and an azide group each attached to an oligonucleotide.

A Sequence Listing appended to the present specification is herein incorporated by reference in its entirety.

BACKGROUND OF THE INVENTION

The CuAAC 'click reaction' ($Cu^I$-catalysed [3+2] alkyne azide cycloaddition) has been used in a vast range of applications due to its high efficiency and orthogonality with almost all other functional groups and solvents. It has found favour in the nucleic acids field as a method of joining together single strands of DNA, cross-linking complementary strands, cyclising single and double strands, labelling oligonucleotides with reporter groups, attaching DNA to surfaces, producing analogues of DNA with modified nucleobases and backbones, synthesizing large chemically modified RNA constructs and creating biochemically active PCR templates. However, $Cu^I$ has undesirable cytotoxicity even at low concentrations so it is not fully compatible with in vivo applications.

Unfortunately the uncatalyzed alkyne-azide cycloaddition (AAC) reaction, in particular the uncatalyzed DNA-templated AAC reaction with terminal alkynes, is exceedingly slow in comparison unless highly activated alkynes are used, and these are unstable in water.

SUMMARY OF THE INVENTION

It is an aim of embodiments of the present invention to provide a method and reagents that are able to join oligonucleotides together using click chemistry in the absence of metal ion catalysis, preferably without Cu(I) catalysis. It is a further aim that this reaction should be performable using reagents that are stable in water.

According to a first aspect of the invention a method for joining together one or more oligonucleotides is provided, said method comprising reacting an alkyne group linked to an oligonucleotide with an azide group linked to an oligonucleotide to form a triazole linkage wherein said alkyne group is a strained alkyne group.

In one embodiment the method comprises ligating together ends of one or more oligonucleotides. In one embodiment the method comprises cross-linking strands of an oligonucleotide duplex.

In the present invention a strained alkyne group may be reacted with an azide group to form a triazole linkage. In one embodiment two oligonucleotides may be joined end to end. End-to-end joining of oligonucleotides is also described herein as ligation. In one embodiment two separate oligonucleotides may be ligated together using the method of the present invention. One advantage of the methods of the present invention may be that oligonucleotide strands may be ligated together without the need for a ligase enzyme. A triazole linkage is formed using the method of the present invention instead of conventional ligation using a ligase enzyme. In the present invention the link formed between the oligonucleotides is a triazole bond instead of a phosphodiester bond.

In one embodiment the linkage may join oligonucleotides across an oligonucleotide duplex. Joining oligonucleotides across an oligonucleotide duplex is described herein as cross-linking. In one embodiment two separate oligonucleotides may be cross-linked across a duplex. In one embodiment two parts of the same oligonucleotide may anneal to form a duplex and the duplex may be cross-linked by a triazole linkage.

In one embodiment a triazole linkage may be formed between the end of an oligonucleotide and a different oligonucleotide.

Ring strain-promoted azide-alkyne [3+2] cycloaddition reaction (the SPAAC reaction) on DNA, for example oligonucleotides, has potential for applications in biology, genomics and nanotechnology. A strained alkyne group is attached to an oligonucleotide and an azide group is attached, either to another oligonucleotide The alkyne group may be strained by being part of a ring, for example a cycloalkyne such as a cyclooctyne. In particular a dibenzocyclooctyne is highly suitable for use attached to oligonucleotides that are used in fast SPAAC reactions with azides attached to oligonucleotides. The conjugated aromatic rings impose ring strain and electron withdrawing properties on the alkyne, making it react very quickly with azides. Substituents to the ring may be used to increase or decrease the reactivity of the alkyne.

In one embodiment the ligation of oligonucleotides or cross-linking of oligonucleotides may be carried out in copper-free and/or copper ion free conditions and more preferably in metal-ion free conditions.

The alkyne group may be sufficiently reactive because of the ring strain to react with the azide group without metal ion catalysis, for example, without $Cu^I$ catalysis. The reaction may proceed in a range of buffers. The reaction may proceed under conditions that are favorable to duplex formation for the oligonucleotides. The reaction may go to completion within a short time scale, for example less than 1 hour, preferably less than 30 minutes, preferably less than 10 minutes, more preferably less than 1 minute, most preferably less than 30 seconds, preferably less than 10 seconds, without $Cu^I$ catalysis. The reaction may occur at room temperature, for example 20° C. The reaction may occur at a temperature between 5 and 40° C., preferably between 10 and 30° C., more preferably between 15 and 25° C., more preferably at about 20° C. The higher the reaction temperature the faster the reaction may proceed.

Suitable cycloalkynes for use may be those that are stable at room temperature and/or stable in water, and/or stable in air. In one embodiment cycloalkynes used may be those that do not require to be stored or reacted under argon.

A SPAAC reaction may be inhibited by metal ions, in particular $Cu^I$. Therefore, it is advantageous to carry out ligation or cross-linking using a SPAAC reaction in $Cu^I$ free conditions, preferably metal ion free conditions. It is also advantageous to carry out the alkyne azide reaction in copper-free conditions because copper inhibits many enzymes. Therefore products of the ligation or cross-linking reaction, where copper is not present, may be used in subsequent reactions without requiring a step to remove copper from solution.

In one embodiment an oligonucleotide linked to an alkyne group and an oligonucleotide linked to an azide group may be joined together in vivo using a SPAAC reaction, for example using endogenous (natural DNA or DNA as a template). This may be advantageous for diagnostic applications, e.g. using fluorescent oligonucleotides, or medical applications, i.e. to inhibit the natural RNA's. Shorter oligonucleotides may be advantageous because they may be able to get into cells better than longer oligonucleotides, therapeutic applications are possible such as joining together short oligonucleotides against the natural RNA target.

In one embodiment the at least one strained alkyne group may be linked to one end of an oligonucleotide. This is advantageous because in one embodiment it allows the oligonucleotide to be ligated end to end with another oligonucleotide having an azide group joined to one end of it. An azide group may be linked to one end of a second oligonucleotide so that the two oligonucleotides may be joined end to end using a SPAAC reaction. One oligonucleotide may have a strained alkyne group joined at each end to ensure that the oligonucleotide ligates to another oligonucleotide which has an azide group at one or both ends rather than circularizing. A series of two, three, four, five, six or more than six oligonucleotides may be joined together end to end using the SPAAC reaction with strained alkyne and azide groups attached to the ends of each oligonucleotide. In one embodiment three, four, five, six or more than six oligonucleotides may be joined together simultaneously end to end using a SPAAC reaction between each oligonucleotide and the adjacent oligonucleotide(s). In one embodiment at least one alkyne group may be linked to the 5' end of the oligonucleotide.

In one embodiment the ligation reaction between the strained alkyne group and the azide group is a template-mediated or templated joining of oligonucleotides. The one or more oligonucleotides may be annealed to a complementary template polynucleotide before the ligation of the oligonucleotides using the SPAAC reaction between the strained alkyne group and the azide group.

In one embodiment the oligonucleotides may comprise DNA, RNA, modified DNA, modified RNA and/or nucleic acid analogues such as PNA. In one embodiment an oligonucleotide may comprise only one out of DNA, RNA, modified DNA, modified RNA and/or nucleic acid analogues such as PNA. In another embodiment an oligonucleotide may comprise a mixture of two or more out of DNA, RNA, modified DNA, modified RNA and/or nucleic acid analogues such as PNA. A strained alkyne group of an azide group may be linked to any type of oligonucleotide.

An example of a monomer that is suitable for 5' addition to oligonucleotides is dibenzocyclooctyne phosphoramidite (DIBO) (monomer A shown in FIG. 6). The resultant 5'-DIBO oligonucleotides may be used in SPAAC reactions for ligation with an azide group attached to a separate oligonucleotide in an end-to-end ligation. Preferably the oligonucleotides may be annealed to a complementary template before end-to-end ligation.

A strained alkyne active ester may be reacted with an aminoalkyl oligonucleotide to add the strained alkyne anywhere in an oligonucleotide. An aminoalkyl group may be added internally away from the ends of an oligonucleotide or to the ends of an oligonucleotide.

A phosphoramidite monomer may be used to add DIBO attached to thymine bases, the sugar attached to thymine bases or the 5'-end of oligonucleotides.

Template-mediated DNA ligation is very fast and a single base pair mismatch is sufficiently destabilising on the duplex to strongly inhibit the reaction. For cross-linking of two strands of a duplex, a single base pair mis-match in the region of the duplex where the strained alkyne group and the azide group are located may strongly inhibit or prevent cross-linking.

For linking of strands end to end, the region of the oligonucleotides where the strained alkyne group and the azide group are located may anneal to an oligonucleotide template to form a region of duplex. The SPAAC reaction may go ahead if the site of the SPAAC reaction is in a section of duplex that has no mis-matches. A single mis-match may inhibit the SPAAC reaction.

For both end to end joining and cross-linking, in order for the SPAAC reaction to go ahead the strained alkyne group and the azide group should preferably be located in a region where the oligonucleotides form a stable duplex. Stability of the duplex is promoted when the oligonucleotides do not have any mis-matches in that region. Stability of the duplex depends on the annealing temperature of the oligonucleotide duplex. One factor that increases stability of the duplex is an increase in the number of CG pairs so the length of mis-match region required for the SPAAC reaction to go ahead may relate to the sequence of the oligonucleotides and the percentage of CG pairs.

The length of the mis-match free region of duplex that is required for the SPAAC reaction to go ahead may be 6 or more base pairs for a sequence that is all CG pairs. The length of the mis-match free region of duplex that is required for the SPAAC reaction to go ahead may be 8 or more base pairs for a sequence that is all AT pairs. Preferably the mis-match free region that surrounds the site of the SPAAC reaction may be 5 or more 6 or more base pairs, preferably 7 or more base pairs, preferably 8 or more base pairs, preferably 10 or more base pairs, preferably 12 or more base pairs, preferably 14 or more base pairs, preferably 20 or more base pairs, preferably 30 or more base pairs. Preferably the mis-match free region that surrounds the site of the SPAAC reaction is long enough to form a stable DNA or RNA duplex.

A templated end to end joining or cross-linking reaction is a reaction that occurs in a section of oligonucleotide duplex wherein the section around the end to end join or cross-link has at least 6, preferably at least 7, preferably at least 8, preferably at least 10 complementary base pairs that form a stable duplex under the conditions where the SPAAC reaction takes place. Templated reactions may take place when the strained alkyne group and the azide group that undergo the SPAAC reaction are each present at least at a concentration of a number of micromolar. For example, the strained alkyne and/or the azide groups may each be present at between 10 and 800 micromolar. In one embodiment the strained alkyne and/or the azide group may each be present at least 10 micromolar, preferably at least 20 micromolar, preferably at least 30 micromolar, preferably at least 40 micromolar, preferably at least 50 micromolar, preferably at least 100 micromolar, preferably at least 150 micromolar, preferably at least 200 micromolar, preferably at least 400 micromolar, preferably at least 800 micromolar. In one embodiment the strained alkyne and/or the azide group may each be present at less than 1 millimolar, preferably less than 800 micromolar, preferably less than 600 micromolar, preferably less than 400 micromolar, preferably less than 200 micromolar.

This is an advantage for genetic analysis applications because the ligation reaction will be significantly slower or will not occur if there is a single mis-match between the oligonucleotides attached to the strained alkyne and azide groups and the template polynucleotide. The ability to detect a single mis-match may provide a sensitive tool for detecting specific nucleotide sequences.

If there is at least one mis-match in the region of duplex surrounding the end to end joining site or the cross-linking site then the reaction is an un-templated reaction. Reactions between two single strands are also un-templated reactions.

Un-templated reactions do not occur under the same conditions. Un-templated reactions may proceed at higher temperature and may take a longer time than templated reactions. Un-templated reactions may proceed at higher concentrations of oligonucleotides. In one embodiment un-templated reactions may occur when the concentration of each of the strained alkyne group and the azide group is in the millimolar range. Preferably the concentration of each of the strained alkyne group and the azide group or the concentration of each oligo having an alkyne group or an azide group attached, is at least 900 micromolar, more preferably the concentration is at least 1 millimolar, more preferably the concentration is at least 1.1 millimolar, preferably the concentration is at least 1.2 millimolar.

Another advantage of performing the ligation using SPAAC under template-mediated conditions is that the ability to control the reaction by using a DNA template means that it is possible to ensure that multiple oligonucleotides can be assembled in the correct order rather than in a random order. In one embodiment each oligonucleotide may be linked to either two alkynes or two azides, one at each end, to prevent the possibility of cyclization.

In one embodiment two, three, four, five, six or more than six oligonucleotides may be annealed to a template to alligne them in the desired order before simultaneously linking each oligonucleotide to the adjacent oligonucleotide(s) using a SPAAC reaction.

In one embodiment the alkyne group is linked to a first oligonucleotide, the azide group is linked to a second oligonucleotide and the first and second oligonucleotides are orientated by binding to a complementary DNA or RNA strand before the ligation takes place.

In one embodiment the alkyne group is linked to one end of a first oligonucleotide, the azide group is linked to one end of a second oligonucleotide and the first and second oligonucleotides are orientated by binding to a complementary DNA or RNA strand before the ligation takes place.

In one embodiment the alkyne group and the azide group are linked to different oligonucleotides, preferably to the ends thereof, and the reaction links the oligonucleotides end to end to form a triazole linkage that is within a single DNA or RNA strand. This is advantageous because it allows a longer oligonucleotide to be formed from two or more oligonucleotides with triazole linkages where each of the original oligonucleotides is joined to another oligonucleotide using the SPAAC reaction.

In another embodiment, the at least one strained alkyne and/or at least one azide group is linked to the oligonucleotide away from the end of the oligonucleotide, for example in a position where it will be directed towards the major groove when the oligonucleotide forms a duplex with another oligonucleotide. This allows joining of the oligonucleotide using SPAAC within the oligonucleotide instead of, and as well as, at the ends. An example of a strained alkyne monomer that may be joined to an oligonucleotide so that, for example, it is attached to the 5-position of the uracil base and is directed into the major groove is shown at C in FIG. 6. Examples of azide monomers that may be linked away from the end of an oligonucleotide, for example, in the major groove are shown F in FIG. 6.

In another embodiment the at least one strained alkyne group is linked away from the end of the oligonucleotide, for example in a position where it will be directed towards the major or minor groove when the oligonucleotide forms a duplex with another oligonucleotide. An example of a strained alkyne monomer that may be joined to an oligonucleotide and, for example, directed towards the major or minor groove is shown at B in FIG. 6. Examples of azide monomers that may be linked away from the end of an oligonucleotide and, for example, in the major or minor groove are shown as D and E in FIG. 6.

Using oligonucleotides that have strained alkyne groups and azide groups within the oligonucleotide away from the ends, the oligonucleotides may be linked across an oligonucleotide duplex to form a triazole linkage between the two strands of the oligonucleotide duplex.

In one embodiment the triazole linkage may be formed in the major groove of an oligonucleotide duplex. In one embodiment triazole linkage is formed in the minor groove of an oligonucleotide duplex. An advantage of cross linking the strands of an oligonucleotide duplex is that it can protect the oligonucleotides from being cleaved by restriction enzymes or other DNA or RNA cleavage enzymes that act on the minor or major groove. In one embodiment at least one alkyne or azide may be joined to one or both ends of an oligonucleotide as well as inside the oligonucleotide sequence away from the ends.

In one embodiment the alkyne group and the azide group react according to the following scheme:

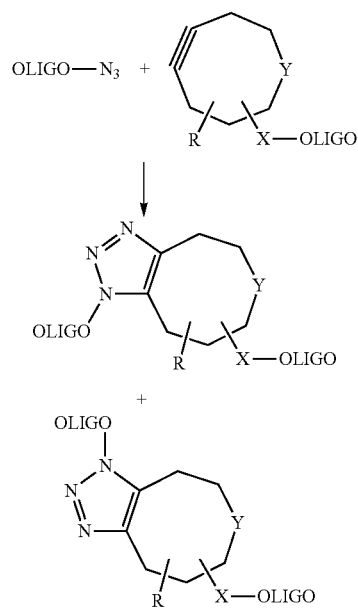

Wherein X is a linker that attaches the strained alkyne group to the oligonucleotide. The length and structure of the linker group X may be varied, Y is carbon or a heteroatom and R is an optional substituent to the ring or electron withdrawing group. The reaction may produce two isomeric triazoles.

This provides a general scheme for the SPAAC reaction between a strained alkyne and an azide, each attached to an oligonucleotide. Two isomeric triazoles are produced.

Strained Alkynes

The strained alkyne used in the present invention may be any strained alkyne group. In one embodiment the strained alkyne may be within a ring structure, for example a cycloalkyne or a cyclic compound where the ring comprises carbon atoms and one or more heteroatoms, for example, one or more nitrogen, sulphur or oxygen atoms in the ring. In the example reaction scheme above "Y" may be a carbon or a heteroatom. The heteroatom may be at any position in the ring. In one embodiment there is one heteroatom in the ring. In one embodiment the strained alkyne group may comprise a 7 to 9 membered ring or a substituted 7 to 9 membered ring. In one embodiment the strained alkyne may comprise an 8 membered ring, or a substituted 8 membered ring. The substituted or unsubstituted 8 membered ring may comprise 8 carbon atoms in the ring or may comprise one or more nitrogen, sulphur or oxygen atoms in the ring in addition to carbon atoms. In one embodiment the strained alkyne group may comprise a cyclooctyne or a substituted cyclooctyne.

It is advantageous to provide a strained alkyne that is reactive enough to perform the SPAAC reaction under laboratory conditions, for example because it can react in water or buffer at normal room temperature, for example 20° C. but that is also stable under laboratory conditions, for example it is stable in water, oxygen stable and stable at normal room temperature.

In one embodiment the strained alkyne group comprises a cyclooctyne or a substituted cyclooctyne. This is advantageous because many cyclooctynes are stable under laboratory conditions and are suitably reactive to carry out the SPAAC reaction in water or buffer at room temperature. The strained alkyne group may comprise a substituted cyclooctyne. This is advantageous because substitutions to the ring can change the reactivity.

In one embodiment the strained alkyne group may comprises an unsubstituted ring, for example the strained alkyne group may be a NSCO group as shown at "1" in FIG. 4.

Substituents to the Ring

In one embodiment the ring comprising the strained alkyne is substituted with one or more groups, shown as R in the reaction scheme above. Substituent groups may be electron-withdrawing groups, groups that increase or decrease the reactivity of the alkyne. In one embodiment a substituent group may comprise one or more conjugated rings. In one embodiment a substituent group may comprise one or more electronegative atoms, for example fluorine.

In one embodiment the ring may be fused with one or more conjugated rings, for example one or more benzene rings.

In one embodiment the strained alkyne group may comprise a ring with one or more substituents to the ring for example, the strained alkyne group may comprise a dibenzocyclooctyne (DIBO) group as shown at "2" and "3" in FIG. 4.

Linkers for 5' and 3' Ends of the Oligonucleotide.

In one embodiment the linker, shown at "X" in the above general scheme links the alkyne group to the 5' end of an oligonucleotide. In one embodiment the linker, shown at "X" in the above general scheme links the alkyne group to the 3' end of an oligonucleotide.

In one embodiment the alkyne group comprises the linker, the ring comprising the strained alkyne (strained alkyne ring) and all of the substituents to the alkyne ring. The linker may comprise all of the structure between the alkyne ring and the oligonucleotide that the strained alkyne group is linked to.

A strained alkyne group or an azide group may be linked to an oligonucleotide by a linker. A linker may be a spacer that allows the strained alkyne and azide to approach each other to react. In order to allow post-synthetic labelling of the oligonucleotide the linker may have a reactive group on it such as an active ester. In this method of labelling the active ester of a strained alkyne, for example a cyclo-octyne group, may be reacted with an amino group that has been added to an oligonucleotide during solid phase synthesis. This amino group can be added at the 5' end, the 3' end or internally on the nucleobases or sugars or phosphates. Alternatively strained alkyne group, for example a cyclo-octyne group, may be added to the oligonucleotide either internally or at the 5' or 3' end during solid-phase oligonucleotide synthesis. In this labelling method the linker attached to the cyclo-octyne must also have a phosphoramidite group attached, or another suitable group for adding monomers to oligonucleotides by the phosphoramidite or H-phosphonate or phosphotriester method of oligonucleotide synthesis. In all the methods described above either single or multiple alkyne groups, for example cyclo-octyne groups can be added to an oligonucleotide.

Linkers may be of different lengths that are appropriate to form the required link. If a spacer is too long it may slow down the reaction between a strained alkyne group and an azide group, if a linker is too short it may inhibit reaction between a strained alkyne group and an azide group as they may not be able to reach each other. A linker may be chosen for each of the strained alkyne and the azide that are to be linked to each other so that the linkers are the appropriate length to allow the strained alkyne group and the azide group to react with each other to join the oligonucleotides. In one embodiment, a hydrophilic spacer such as (CH2CH2O)n might be preferable to a hydrophobic spacer such as (CH2)n.

The following strained alkyne groups provide examples of strained alkyne groups that can be added to the end of oligonucleotides as active esters or phosphoramidite monomers.

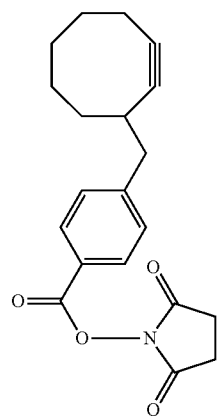

NSCO N-hydroxysuccinimidyl carbonate

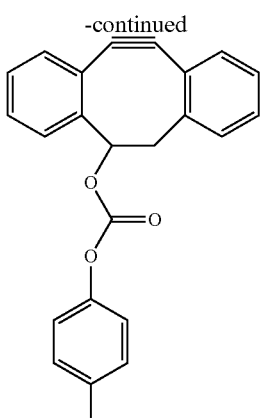

DIBO p-nitrophenyl carbonate

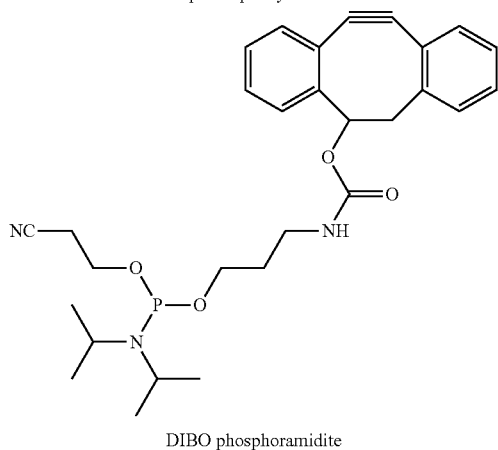

DIBO phosphoramidite

DIBO phosphoramidite is suitable for insertion during solid phase oligonucleotide synthesis and can be inserted at the 5' end of an oligonucleotide.

DIBO and DIBO phosphoramidite may be preferred to NSCO because DIBO reacts more quickly than NSCO in a templated SPAAC reaction under laboratory conditions.

Some linkers may be used either for linking a strained alkyne group to an oligonucleotide or for linking an azide group to an oligonucleotide.

Linkers for Joining within Oligonucleotides

As used herein the term "strained alkyne group" may comprise the ring that comprises a carbon to carbon triple bond and may also comprise substituent groups. The term strained alkyne group may also include a linker used to join the strained alkyne ring to a nucleotide or oligonucleotide. The linker may also be discussed separately.

The term "azide group" may comprise the azide and any substituent groups. The term "azide group" may also include a linker that is used to join the group to a nucleotide or oligonucleotide. The linker may also be discussed separately.

A strained alkyne group and an azide group may be covalently linked within an oligonucleotide away from the ends of the oligonucleotide. In one embodiment the strained alkyne group or a linker attached to the strained alkyne group is not added to the free phosphate group at the 5' end of the oligonucleotide and it is not added to the free OH group at the 3' end of the oligonucleotide.

The strained alkyne group or an azide group may be covalently attached to a nucleobase for example to a thymidine, adenine, cytosine, guanine or uracil of a nucleotide or nucleoside. The strained alkyne group may be attached to the nucleobase of a deoxyribonucleotide or a ribonucleotide or a nucleoside analogue. The strained alkyne group may be attached to the nucleobase of a deoxyribonucleotide or ribonucleotide before it is attached to other deoxyribonucleotides or ribonucleotides to form an oligonucleotide. In another embodiment a strained alkyne group may be attached to a nucleobase that is part of an oligonucleotide.

A strained alkyne group or an azide group may be attached to the sugar moiety for example in the 2'-position, or to the phosphate group. The position of attachment influences whether the triazole linker is likely to stretch across the major or minor groove but it will not absolutely determine this. i.e. some of the linkers can stretch across either groove, particularly the longer ones.

The following strained alkyne groups are examples of groups that are suitable for adding within an oligonucleotide away from the ends of the oligonucleotide.

2'-DIBO dT below is suitable for attaching in the minor or major groove.

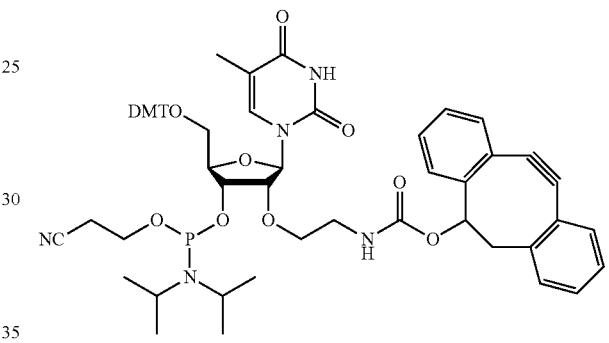

5-DIBO propargyl dT below is suitable for attaching to the major groove.

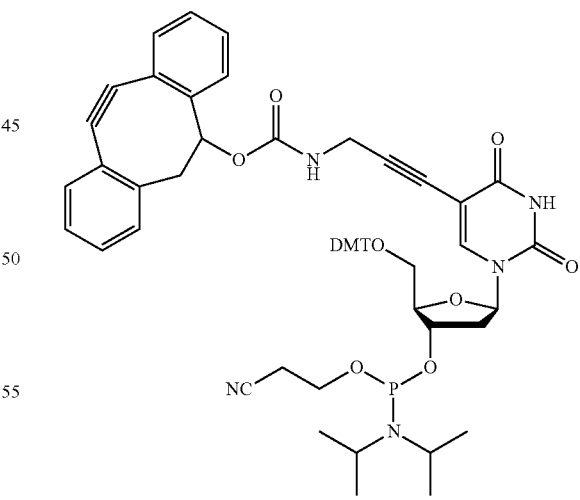

Joining Oligonucleotides

In one embodiment the ends of two oligonucleotides may be ligated together end to end as shown in the general scheme at b, c and d in FIG. 2. Preferably the end-to-end ligation is a templated ligation reaction. Preferably the parts of the strands that are going to be ligated together are annealed to a complementary oligonucleotide before being ligated together using a SPAAC reaction. Annealing to an oligonucleotide template may keep the ends in the correct position in order for the ligation to occur.

In one embodiment the strained alkyne group and the azide group that are used may be groups that react together under conditions that are favorable for the oligonucleotides that are joined to the alkyne group and the azide group to anneal to a template oligonucleotide. In one embodiment reaction conditions such as the temperature, ionic strength and pH of the reaction solution are favorable for complementary oligonucleotides to anneal to each other.

A strained alkyne group or an azide group may be added to the 5' or 3' end of an oligonucleotide molecule. The strained alkyne group or the azide group, or a linker attached to the strained alkyne group or the azide group, may be added to the 3' end of the oligonucleotide to form a covalent bond by the active ester or phosphoramidite or H-phosphonate method described above.

In one embodiment two strands of an oligonucleotide duplex may be cross-linked using a SPAAC reaction. In one embodiment a strained alkyne group may be attached to one oligonucleotide away from the ends. An azide group may be attached to a complementary oligonucleotide away from the ends. When the oligonucleotides are annealed together the strained alkyne group and the azide group may undergo a SPAAC reaction to cross-link the oligonucleotides.

FIG. 2 shows, at a), a schematic diagram of cross-linking two complementary DNA or RNA strands or a DNA strand with an RNA strand, or a modified DNA or RNA strand to any of the above, using a SPAAC reaction. The strained alkyne group and the azide group are within the oligonucleotides away from the ends and react with each other across the polynucleotide duplex to form a triazole linkage across the minor groove or across the major groove. The alkyne group and the azide group may be linked to the strands at positions that will be adjacent to when two complementary oligonucleotides anneal to each other. These positions may have complementary base pairs or may have mis-matched base pairs or base analogues. Miss-matched base pairs at these positions may slow down the reaction.

In one embodiment the linkers that attach the alkyne group or the azide group to the oligonucleotide may be long enough to allow the alkyne and azide groups to cross-link nucleotides that are not on adjacent or opposite base pairs when the two oligonucleotides anneal to each other. In one embodiment the alkyne group and the azide group are attached, within complementary strands, to nucleotide residues that are separated by one base pair, preferably separated by up to 2 base pairs, preferably separated by up to 3 base pairs, preferably separated by up to 5 base pairs, preferably separated by up to 10 base pairs, preferably separated by up to 50 base pairs. In one embodiment the strained alkyne group and the azide group are on the opposing bases of a base pair.

An oligonucleotide is a molecule of DNA or RNA or a combination of DNA and RNA having at least two, preferably at least 5, more preferably at least 10, more preferably at least 25, more preferably at least 50, more preferably at least 100, more preferably at least 200 base pairs. In the present invention an oligonucleotide may have a triazole linkage within one strand, for example as a result of an alkyne-azide cycloaddition reaction within one strand of a DNA or RNA duplex.

In one embodiment one of the oligonucleotides used in the SPAAC reaction is attached to a solid phase.

In one embodiment one or more of the oligonucleotides used in the SPAAC reaction are labelled internally with azide derivatives of one or more reporter groups such as fluorescent dyes or biotin, for example using the DIBO dT phosphoramidite monomers.

In one embodiment two or more oligonucleotides, each attached to a nanoparticle, protein or biomolecule are joined using the SPAAC reaction. The two nanoparticles, proteins or biomolecules are thereby linked together as a result of the linking of the oligonucleotides.

In one embodiment, for the SPAAC reaction to proceed and ligate two oligonucleotides they must be annealed to a template with a high degree of complementarity to the oligonucleotides. In one embodiment a single mis-match between the template and the oligonucleotide is sufficient to inhibit the ligation.

The requirement for an exactly complementary template may be useful for genetic analysis applications.

The use of the SPAAC reaction may also be advantageous because it requires a template that is exactly complementary to the sequence of the probe regions on the open circle probe. The SPAAC reaction will not proceed if there is a single mis-match between the probe and the target sample. Therefore this technique can identify the amount of target sequence in a sample with a high degree of precision.

In one embodiment an oligonucleotide attached to a strained alkyne group and/or an oligonucleotide attached to an azide group may also comprise a fluorophore. In one embodiment the alkyne and/or the azide group may comprise a fluorophore. In one embodiment one or more of the oligonucleotides may comprise a fluorophore in addition to the alkyne or azide group.

In one embodiment the reaction of the strained alkyne group with the azide group brings two fluorophores close enough together to cause a change in the fluorescence properties of one or more of the fluorophores, for example quenching of fluorescence or fluorescence energy transfer (FRET) Examples of pairs of compounds that could be used to label oligonucleotides are fluorescein and tetramethylrhodamine, or cy3 and cy5.

The following oligonucleotides joined to strained alkyne or azide groups may, for example, be useful in the present invention:

An oligonucleotide linked to a strained alkyne group wherein the strained alkyne group comprises a substituted or un-substituted cyclooctyne;

An oligonucleotide linked to a strained alkyne group, wherein the strained alkyne group comprises a cyclooctyne having at least one heteroatom in the ring;

An oligonucleotide linked to a strained alkyne group, wherein said strained alkyne group is a DIBO group;

An oligonucleotide linked to a strained alkyne group, or an azide group wherein the strained alkyne group or the azide group is linked to the end of the oligonucleotide.

An oligonucleotide linked to a strained alkyne group or an azide group, wherein the strained alkyne group or the azide group is linked to the 5' end of the oligonucleotide.

An oligonucleotide wherein a strained alkyne group is linked to a first end of the oligonucleotide and a second strained alkyne group is linked to a second end of the oligonucleotide.

An oligonucleotide wherein an azide group is linked to a first end of the oligonucleotide and a second azide group is linked to a second end of the oligonucleotide An oligonucleotide linked to a strained alkyne group or an azide group, wherein the strained alkyne group or the azide group is linked away from the end of the oligonucleotide in the major groove.

An oligonucleotide linked to a strained alkyne group or an azide group, wherein the strained alkyne group or the azide group is linked away from the end of the oligonucleotide in the minor groove.

An oligonucleotide linked to a strained alkyne group, wherein the alkyne group is selected from the following cyclooctyne or dibenzocyclooctyne groups and is linked to the oligonucleotide through the groups shown:

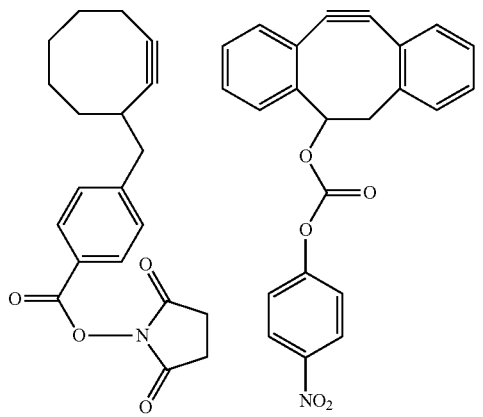

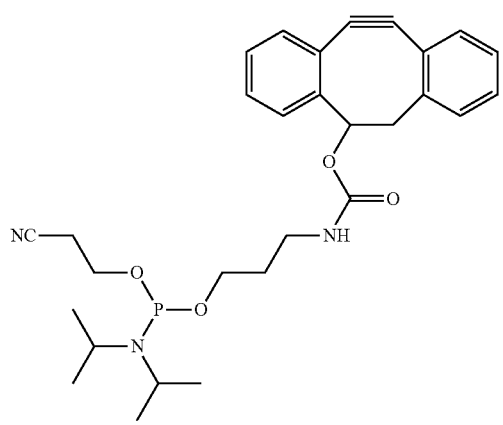

An oligonucleotide wherein the alkyne group is selected from the following cyclooctyne or dibenzocyclooctyne groups and is linked to the oligionucleotide through the groups shown:

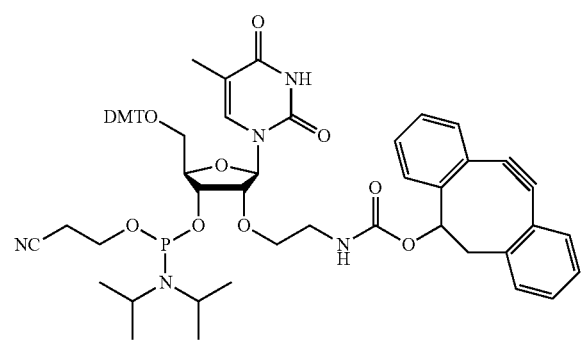

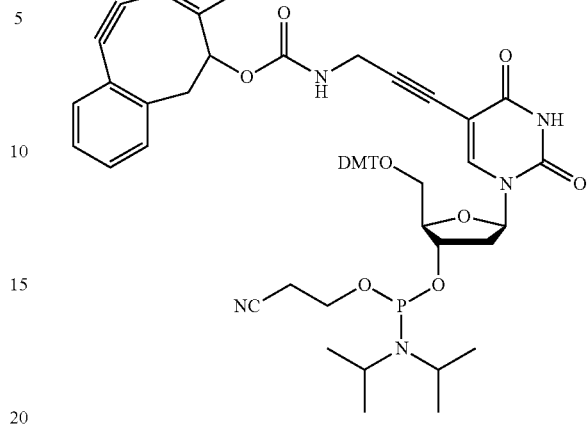

A double stranded DNA, double stranded RNA or double stranded hybrid of or modified DNA or RNA, wherein the two strands are cross-linked with at least one triazole linkage.

A double stranded DNA, double stranded RNA or double stranded hybrid of or modified DNA or RNA, wherein the two strands are cross-linked with at least one triazole linkage in the major groove.

A double stranded DNA, double stranded RNA or double stranded hybrid or modified DNA or RNA, wherein the two strands are cross-linked with at least one triazole linkage in the minor groove.

Methods of the present invention may be useful in attachment & fabrication via solid phases (oligo printing; 3D nanoassemblies); Possibilities in nanotechnology to produce covalently fixed DNA-nanoconstructs that can be purified and used as building blocks in the synthesis of larger nanoconstructs.

Methods and oligonucleotides of the present invention may be used in applications such as FISH (fluorescence in situ hybridization) to produce oligonucleotide probes with long tails with multiple fluorescent groups that will produce unique colors for applications such as chromosome paints, e.g. to analyse for translocations in cancer diagnostics. The long fluorescent tails may be synthesised separately and attached onto specific oligonucleotide probe sequences using the oligonucleotide joining methods of the present invention, so that all the probes for a particular regions of a specific chromosome have a unique color and probes for other regions/chromosomes have different unique colors. The fluorescent tags could be used to join to oligonucleotide probes for other applications that require oligonucleotide probes.

Synthesis of oligonucleotide duplexes with both ends capped (end-sealed duplexes). Oligonucleotides functionalised with 3' and 5'-DIBO can be reacted with complementary oligonucleotides that are functionalised with 3' and 5'-azide. The reaction produces "end sealed" duplexes with triazole linkers at each end of the duplex. The sequence of the duplex can be chosen to be a binding site for a transcription factor. Alternatively, modified, mutagenic or epigenetic bases can be incorporated into an end sealed duplex such that it is a substrate for a DNA repair enzyme or another enzyme involved in DNA processing. End sealed duplexes can be used in vivo as decoys for enzymes such as those mentioned above, and as such they have potential biomedical applications. The advantages of this approach are:

Very short end sealed oligonucleotides (even those with only two base pairs) form stable duplexes under physiological conditions because the process of duplex formation is intramolecular. In contrast, the formation of normal duplexes is an intermolecular process and is therefore dependent on DNA concentration. Consequently end sealed duplexes have much higher thermal stability than normal duplexes and can therefore be shorter without separating into two unpaired strands.

Another consequence of the end sealing is that the two strands of the duplex cannot come apart in vivo as they are chemically linked (unlike normal duplexes).

Short oligonucleotides are more readily taken up into cells than long oligonucleotides. Hence end sealed duplexes are more likely to be delivered into cells as they can be much shorter and still be active as double stranded decoys.

End sealed duplexes have greater in vivo stability than normal duplexes because they do not have free ends that can be digested by DNase enzymes (3'- or 5'-exonuclease enzymes).

Moreover, the click ligation reaction can be performed on a large scale to provide decoys for potential therapeutic use. This would not be possible with enzymatic ligation due to the high cost of ligase enzymes.

BRIEF DESCRIPTION OF THE DRAWINGS

There now follows by way of example only a detailed description of the present invention with reference to the accompanying drawings, in which;

FIG. 2 shows a) a schematic diagram of cross-linking two complementary DNA or RNA, or a DNA with an RNA strand or a modified DNA or RNA strand or nucleic acid analogue with any of the above using a SPAAC reaction. b) a schematic diagram of template-mediated ligation of two DNA or RNA strands using a SPAAC reaction, c) an example of template mediated ligation and d) a schematic diagram of use of SPAAC to join together molecules such as proteins, nanoparticles or magnetic beads;

FIG. 6 shows monomers and reagents for labelling oligonucleotides with DIBO for use in the ring strain-promoted azide-alkyne [3+2] cycloaddition reaction (SPAAC) for DNA (or modified DNA) strand ligation and DNA strand cross linking;

DETAILED DESCRIPTION

Synthesis of Monomers

Figure 1:
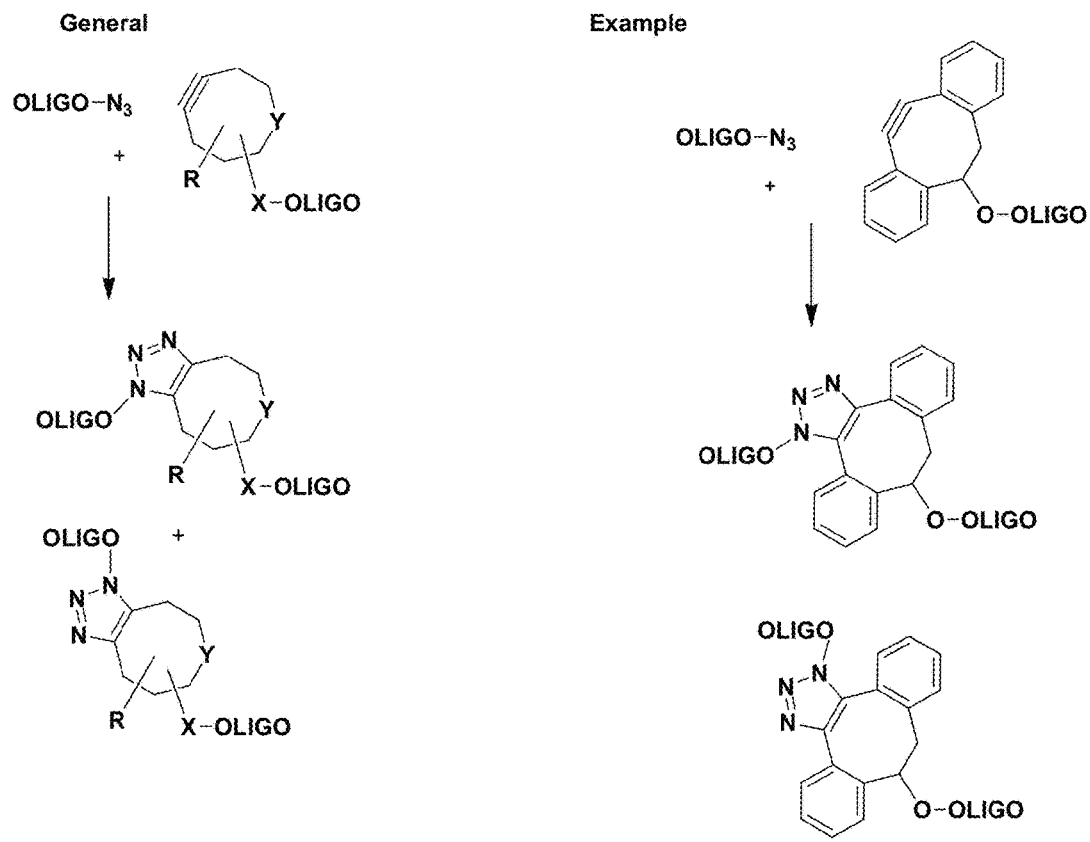
FIG. 1 shows a general reaction scheme and a specific example for the reaction of an alkyne linked to an oligonucleotide with an azide group linked to an oligonucleotide to form a triazole linkage which can be in one of two isomeric forms.
Figure 3:
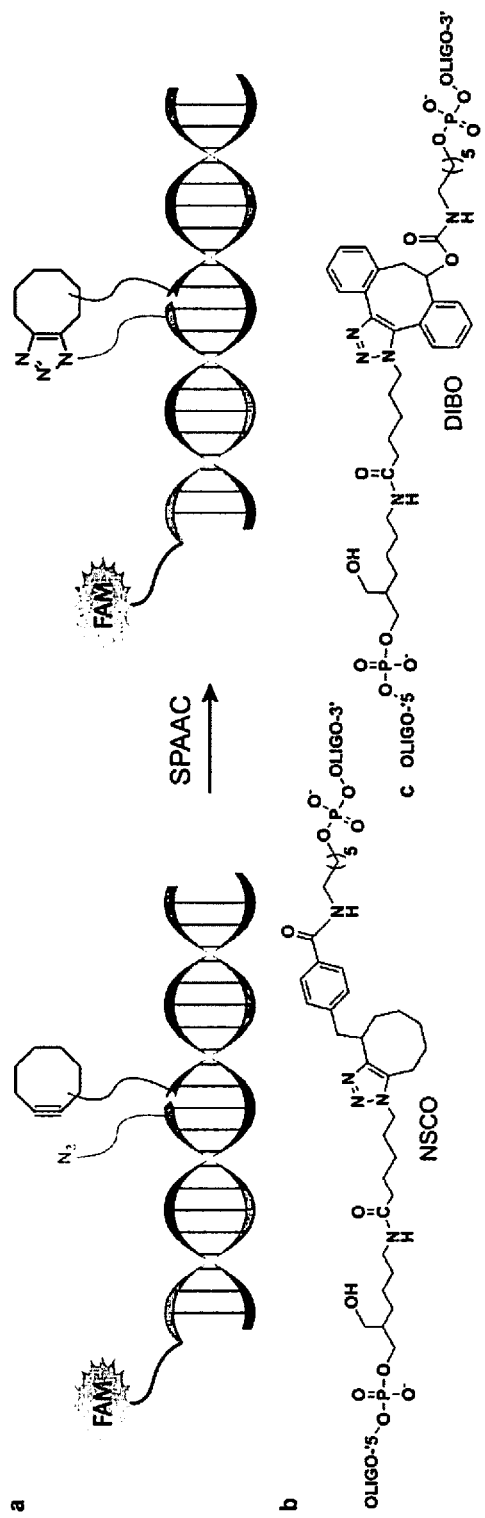
FIG. 3 shows a) an example of SPAAC DNA ligation between azide-labelled and cyclooctyne-labelled oligonucleotides, a schematic of the reaction (FAM=6-carboxyfluorescein), b) and c) show chemical structures of NSCO and DIBO alkynes respectively at the ligation point.

General Information:

All reagents were purchased from Aldrich, Fluka, Avocado, Acros Organics or Baseclick GmbH (www.baseclick.eu) and used without purification with the exception of the following solvents, which were purified by distillation: THF (over sodium wire), DCM, DIPEA, $Et_3N$ and pyridine (over calcium hydride). Chemical transformations were carried out under an atmosphere of argon using oven-dried glassware. Thin layer chromatography (TLC) was performed using Merck Kieselgel 60 F24 silica gel plates (0.22 mm thickness, aluminium backed) and the compounds were visualised by irradiation at 254 nm or by staining with ceric sulfate or ninhydrin solution. Column chromatography was carried out under argon pressure using Fisher Scientific DAVISIL 60 Å (35-70 micron) silica.

$^1$H NMR spectra were measured at 300 MHz on a Bruker AC300 spectrometer or at 400 MHz on a Bruker DPX400 spectrometer. The $^{13}$C NMR spectra were measured at 75 MHz and 100 MHz respectively on the same spectrometers. The $^{31}$P NMR spectrum was recorded on a Bruker AC300 spectrometer at 121 MHz. Chemical shifts are given in ppm relative to tetramethylsilane, and J values are quoted in Hz. All spectra were internally referenced to the appropriate residual undeuterated solvent signal, assignment of the compounds was aided by COSY ($^1$H-$^1$H) and HMQC/HMBC ($^1$H-$^{13}$C) experiments.

All the low-resolution mass spectra were recorded using electrospray ionisation on a Fisons VG platform instrument or a Waters ZMD quadrupole mass spectrometer in HPLC grade acetonitrile. High-resolution mass spectra were recorded in HPLC grade acetonitrile using electrospray ionisation on a Bruker APEX III FT-ICR mass spectrometer. Electrospray Mass spectrometry of oligonucleotides was recorded in water using a Bruker micrOTOF™ II focus ES-TOF MS instrument in ES⁻ mode.

Synthesis of the DIBO monomer 3: (i) 3-amino-1-propanol, DCM, $Et_3N$, 88% yield (ii) 2-cyanoethyl-N,N-diisopropyl chlorophosphoramidite, DCM, DIPEA, 73% yield.

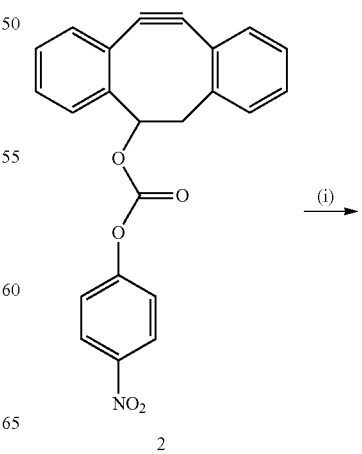

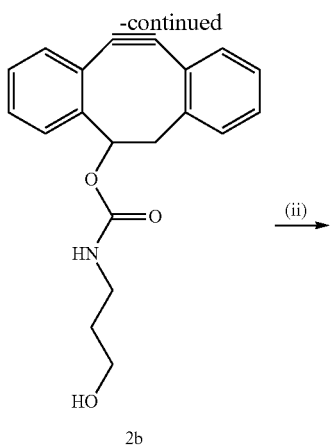

2b

3-{[N-(3-hydroxypropyl)carbamoyl]oxy}-7,8-didehydro-1,2:5,6-dibenzocyclooctyne (2b)

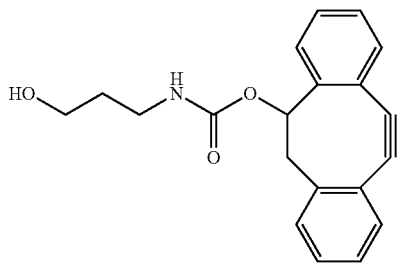 [SMILES: O=C(NCCCO)OC1Cc2ccccc2C#Cc2ccccc21]

To a solution of active ester 2 (0.17 g, 0.44 mmol) in anhydrous DCM (5 mL) was added anhydrous Et₃N (0.4 mL) followed by 3-amino-1-propanol (0.04 mL, 0.53 mmol) under an argon atmosphere at room temperature. The reaction mixture was stirred for 30 min at room temperature, diluted with DCM (10 mL) and the resulting mixture was extracted with saturated brine (2×10 mL). The combined extracts were dried over Na₂SO₄, and the solvent was removed in vacuo. The crude product was purified by column chromatography (50-65% EtOAc/Hexane) to give compound 2b as a white solid (0.13 g, 0.39 mmol, 88%). R$_f$ 0.29 (65% EtOAc/Hexane).

¹H NMR (400 MHz, CDCl₃) δ 7.42 (d, 1H, J=7.6 Hz, CH—Ar), 7.37-7.11 (m, 7H, CH—Ar), 5.44 (m, 1H, CHOC=O), 3.77-3.52 (m, 2H, CH₂OH), 3.29 (m, 2H, NHCH₂), 3.09 (dd, 1H, J=14.9, 1.8 Hz, CH₂), 2.85 (dd, 1H, J=15.2, 3.5 Hz, CH₂), 2.26 (br. s., 1H, OH), 1.65 (m, 2H, NHCH₂CH₂CH₂OH).

¹³C NMR (100 MHz, CDCl₃) δ 156.7 (C=O), 152.2 (C—Ar), 151.2 (C—Ar), 130.2 (CH—Ar), 128.4 (CH—Ar), 128.2 (CH—Ar), 127.4 (CH—Ar), 127.4 (CH—Ar), 126.6 (CH—Ar), 126.3 (CH—Ar), 124.1 (C—Ar), 123.9 (CH—Ar), 121.6 (C—Ar), 113.3 (C—Ar), 110.2 (C—Ar), 77.1 (CHOC=O), 59.9 (CH₂OH), 46.5 (CH₂), 38.1 (HNCH₂), 32.9 (HNCH₂CH₂CH₂OH).

LRMS [ES⁺, MeCN]: m/z (%): 322.2 ([M+H]⁺, 64%), 344.2 ([M+Na]⁺, 50%).

HRMS [ES⁺]: C₂₀H₁₉NNaO₃ requires 344.1263 found 344.1252.

3-(N-{3-O-[(2-cyanoethyl-N,N diisopropyl)phosphoramidyl]propyl}carbamoyloxy)-7,8-didehydro-1,2:5,6-dibenzocyclooctyne (3)

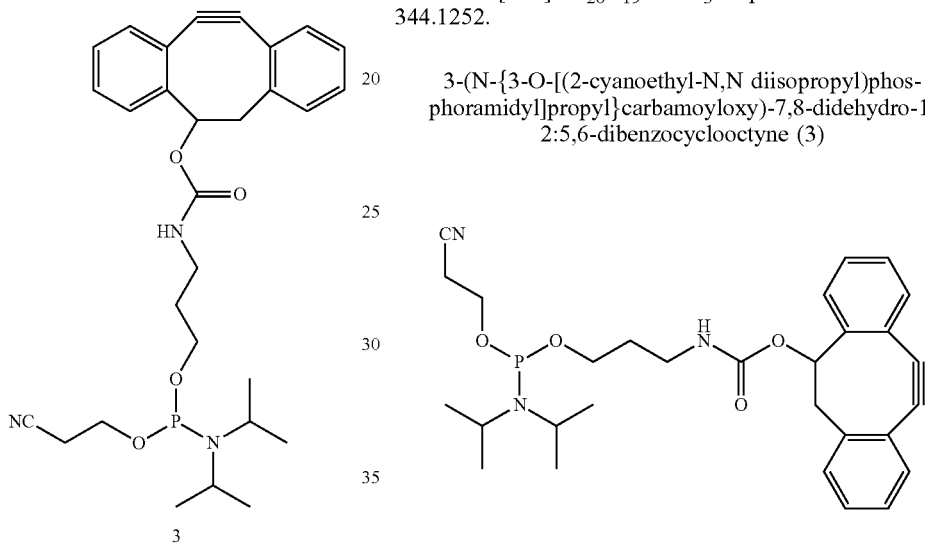

Alcohol 2b (0.9 g, 2.8 mmol) was co-evaporated with anhydrous DCM (3×3 mL) before being dissolved in anhydrous DCM (20 mL) followed by the addition of anhydrous DIPEA (1 mL, 5.6 mmol). 2-Cyanoethyl-N,N-diisopropylchlorophosphoramidite (0.75 mL, 3.36 mmol) was added dropwise, and the reaction mixture was left to stir at room temperature for 40 min, then transferred under argon into a separating funnel that contained degassed DCM (30.0 mL). The mixture was washed with degassed saturated aqueous KCl (30.0 mL), and the organic layer was separated, dried over Na₂SO₄, filtered and the solvent removed in vacuo. The phosphoramidite product was purified by column chromatography under argon pressure (40% EtOAc/Hexane, 0.5% pyridine) to give the title compound 3 (1.07 g, 2.04 mmol, 73%). R$_f$ 0.26 (30% EtOAc/Hexane).

³¹P NMR (121 MHz, CD₃CN) δ 148.5

¹H NMR (400 MHz, CD₃CN) δ 7.58 (d, 1H, J=7.6 Hz, CH—Ar), 7.46-7.29 (m, 7H, CH—Ar), 6.05-5.90 (m, 1H, NH), 5.36 (br. s., 1H, CHOC=O), 3.86-3.69 (m, 2H, POCH₂), 3.76-3.63 (m, 2H, CH₂O), 3.68-3.54 (m, 2H, CH(CH₃)₂), 3.31-3.09 (m, 3H, NHCH₂ & CH₂), 2.83 (dd, 1H, J=14.9, 3.8 Hz, CH₂), 2.63 (t, 2H, J=6.1 Hz, CH₂CN), 1.86-1.70 (m, 2H, NHCH₂CH₂CH₂O); 1.26-1.09 (m, 12H, (CH(CH₃)₂).

LRMS [ES⁺, MeCN] m/z (%): 544.3 ([M+Na]⁺, 100%).

HRMS [ES⁺]: C₂₃H₃₆N₃NaO₄P requires 544.2341 found 544.2335.

Synthesis of the NSCO active ester 1: (i) EDC, N-hydroxysuccinimide, DIPEA, DCM, 51% yield.

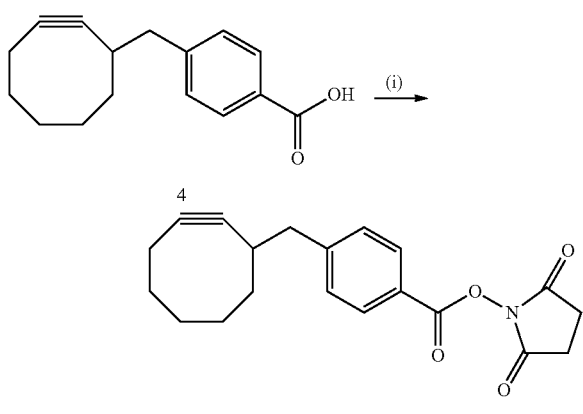

2,5-Dioxopyrrolidin-1-yl 4-(cyclooct-2-ynylmethyl)benzoate (1)

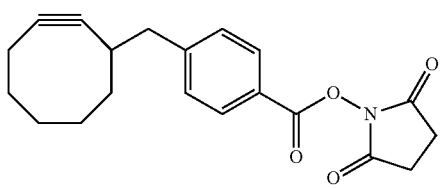 [SMILES: O=C(ON1C(=O)CCC1=O)c1ccc(CC2C#CCCCCC2)cc1]

N-(3-Dimethylaminopropyl)-N'-ethylcarbodiimide hydrochloride (EDC.HCl) (0.39 g, 2.06 mmol) was added with stirring to a suspension of carboxylic acid 4 (0.2 g, 0.82 mmol), N,N'-diisopropylethylamine (DIPEA) (0.51 mL, 2.96 mmol) and N-hydroxysucinimide (0.24 g, 2.06 mmol) in DCM (7.0 mL) over molecular sieves. The reaction was left to stir at room temperature for 4 hr. The suspension was then diluted with DCM (40 mL) and washed with dilute HCl (20 mL, 1M) then distilled water (3×30 mL). The aqueous layer was back-extracted by DCM (1×20 mL). The combined extracts were dried over $Na_2SO_4$, and the solvent was removed in vacuo. The crude product was purified by column chromatography (Pet Ether:Toluene:EtOAc 3:1:0.5) to give compound 1 as a white solid (0.14 g, 50.6%). $R_f$ 0.26 (40% EtOAc/Petroleum Ether).

$^1$H NMR (400 MHz, $CDCl_3$) δ 8.06 (d, 2H, J=8.0 Hz, C$\underline{H}$—Ar), 7.37 (d, 2H, J=8.5 Hz, C$\underline{H}$—Ar), 2.90 (br s, 4H, 2×C$\underline{H_2}$), 2.82-2.67 (m, 2H, C$\underline{H_2}$), 2.81-2.72 (m, 1H, C$\underline{H}$), 2.24-1.72 (m, 7H, C$\underline{H_2}$), 1.67-1.57 (m, 1H, C$\underline{H_2}$), 1.48-1.38 (m, 2H, C$\underline{H_2}$).

$^{13}$C NMR (100 MHz, $CDCl_3$) δ 169.3 (N$\underline{C}$=O), 161.8 (O$\underline{C}$=OC—Ar), 148.1 (Ar—$\underline{CC}$=O), 130.6 ($\underline{C}$—Ar), 129.5 ($\underline{C}$—Ar), 122.9 ($CH_2\underline{C}$—Ar), 95.7 ($\underline{C}$≡C), 95.3 (C≡$\underline{C}$), 41.7 ($\underline{CH_2}$), 40.4 ($\underline{CH_2}$), 36.4 ($\underline{CH}$), 34.7 ($\underline{CH_2}$), 29.9 ($\underline{CH_2}$), 28.44 ($\underline{CH_2}$), 25.7 ($\underline{CH_2}$), 20.8 ($\underline{CH_2}$).

LRMS [ES$^+$, MeCN] m/z (%): 403.3 ([M+MeCN+Na]$^+$, 100%).

HRMS [ES$^+$]: $C_{20}H_{21}N_1NaO_4$ requires 362.1363 found 362.1357.

Oligonucleotide Synthesis and Azide Labelling:

Standard DNA phosphoramidites, solid supports, and additional reagents were purchased from Link Technologies Ltd or Applied Biosystems (UK) Ltd. For 5'-amino group addition TFA-protected aminohexyl phosphoramidite was used and for 3'-amino group addition TFA-protected aminolink C7-solid support was employed (both from Link Technologies). Oligonucleotides were synthesized on an Applied Biosystems 394 automated DNA/RNA synthesizer using a standard 0.2 or 1.0 μmol phosphoramidite cycle of acid-catalyzed detritylation, coupling, capping, and iodine oxidation. Stepwise coupling efficiencies and overall yields were determined by the automated trityl cation conductivity monitoring facility on the DNA synthesizer and in all cases were >98.0%. All β-cyanoethyl phosphoramidite monomers were dissolved in anhydrous acetonitrile to a concentration of 0.1 M immediately prior to use. The coupling times were 35 seconds for normal A, G, C, and T monomers and the coupling time for the alkyne phosphoramidite monomer 3 and 5'-TFA-aminohexyl phosphoramidite was extended to 6 min. Cleavage of oligonucleotides from the solid support and deprotection was achieved by exposure to concentrated aqueous ammonia solution for 5 hr at 55° C. For the modified ODN-4 containing DIBO phosphoramidite monomer 3, N(4)-acetyl dC, N(2)-dmf dG and N(6)-benzoyl dA amidites were used (fast deprotecting monomers), and deprotection was achieved by exposure to concentrated aqueous ammonia solution for 1 hr at 55° C. The oligonucleotides were subsequently heated in ammonia for prolonged periods (>5 hr) to determine their stability. The oligonucleotides were gel-filtered using disposable NAP-10 columns (GE Healthcare) according to the manufacturer's instructions then freeze-dried before labelling. For azide-labelling, 6-azidohexanoic acid NHS ester[1] (1 mg) in DMSO (80 μL) was added to the freeze-dried 3'-amino-modified oligonucleotide (1.0 μmol) in 80 μL of 0.5 M $Na_2CO_3$/$NaHCO_3$ buffer at pH 8.75 (4 hr, room temperature) to give ODN-3. The fully-labelled oligonucleotides were gel-filtered using disposable NAP-10 sephadex columns (GE Healthcare) and purified by reversed-phase HPLC.

Labelling of Oligonucleotide with Alkyne NSCO (1)

The NSCO active ester 1 (2 mg) in DMF (160 μL) was added post-synthetically to the freeze dried amino-modified oligonucleotide (1.0 μmol) in 0.5 M $Na_2CO_3$/$NaHCO_3$ buffer (160 μL) at pH 8.75 (4 hr, room temperature), The fully-labelled oligonucleotide (ODN-2) was desalted by using NAP-10 sephadex columns and purified by reversed-phase HPLC.

Labelling of Oligonucleotide with Alkyne DIBO (2)

The DIBO active ester 2 (1 mg) in DMF (80 μL) was added post-synthetically to the freeze dried amino-modified oligonucleotide (1.0 μmol) in 0.5 M $Na_2CO_3$/$NaHCO_3$ buffer (80 μL) at pH 8.75 (4 hr, 55° C.), The fully-labelled oligonucleotide (ODN-1) was desalted using a NAP-10 sephadex column and purified by reversed-phase HPLC.

General Method for the Templated and Non-Templated Ligation Reactions in the Absence of Cu$^I$ (SPAAC)

A solution of template (ODN-5) and azide (ODN-3) oligonucleotides (0.2 nmol of each) in 0.2 M NaCl (100 μL) was annealed for 30 min at room temperature, after which the alkyne oligonucleotide (0.2 nmol) was added. The reaction mixture was left at room temperature for a specified period of time before adding 50 μL formamide and loading directly onto a 20% polyacrylamide/7 M urea gel. It was electrophoresed at a constant power of 20 W for 3 hr in 0.09 M Tris-borate-EDTA buffer. The gel-purified product was analysed and characterised by mass spectrometry. For the non-templated reactions the same conditions were used without the addition of the template oligonucleotide.

Ligation Reactions in the Presence of Cu$^I$

A solution of template ODN-5 and azide ODN-3 (0.2 nmol of each) in 0.2 M NaCl (50 μL) was annealed for 30 min at room temperature. In the meantime tris-hydroxypropyl triazole ligand[2] (28 nmol in 42 μL 0.2 M NaCl), sodium ascorbate (40 nmol in 4 μL 0.2 M NaCl) and $CuSO_4.5H_2O$ (4 nmol in 4.0 μL 0.2 M NaCl), were added under argon to the alkyne oligonucleotide (0.2 nmol) which was added immediately to the solution containing the template and azide oligonucleotides. The reaction mixture was kept under argon at room temperature for the desired time before analysing the reaction by adding 50 μL formamide and loading directly onto a 20% polyacrylamide electrophoresis gel.

In another experiment, $Cu^I$ solution was added to the azide oligonucleotide in the presence of the template oligonucleotide then the alkyne oligonucleotide was added. This gave similar results to adding the $Cu^I$ solution to the alkyne oligonucleotide then adding this mixture to the azide and template oligonucleotides.

Ligation Reactions in the Presence of $Cu^I$ and EDTA

Template ODN-5 and azide ODN-3 (0.2 nmol of each) in 0.2 M NaCl (50 μL) were annealed for 30 min at room temperature. In the meantime tris-hydroxypropyl triazole ligand (28 nmol in 42 μL 0.2 M NaCl), sodium ascorbate (40 nmol in 4 μL 0.2 M NaCl) and $CuSO_4.5H_2O$ (4 nmol in 4.0 μL 0.2 M NaCl), were added under argon to the alkyne oligonucleotide (0.2 nmol) and left at room temperature for 10 min before adding EDTA (400 nmol in 4 μL 0.2 M NaCl). The mixture was left for 10 min at room temperature then added to the solution containing the template and azide oligonucleotides. The reaction mixture was kept under argon at room temperature for 30 min before adding 50 μL formamide and loading directly onto a 20% polyacrylamide gel for electrophoresis.

Binding of Cyclooctyne to $Cu^I$

Tris-hydroxypropyl triazole ligand (28 nmol in 57 μL 0.2 M NaCl), sodium ascorbate (40 nmol in 2 μL 0.2 M NaCl) and $CuSO_4.5H_2O$ (4 nmol in 1 μL 0.2 M NaCl), were added to the alkyne oligonucleotides (0.2 nmol in 440 μL 0.2 M NaCl) under argon and the reaction was left at room temperature for 20 min before the reagents were removed using a NAP-10 sephadex gel-filtration column. The aqueous solution was then freeze dried overnight before re-dissolving the solid in 100 μL 0.2 M NaCl which was then added to template ODN-5 and azide ODN-3 (0.2 nmol of each). The reaction mixture was then left at room temperature for 30 min before adding 50 μL formamide and loading directly onto a 20% polyacrylamide gel for electrophoretic analysis of the reactions. For the non-templated reactions the same conditions were used without addition of the template oligonucleotide.

Ligation of Strands End to End

Figure 4:
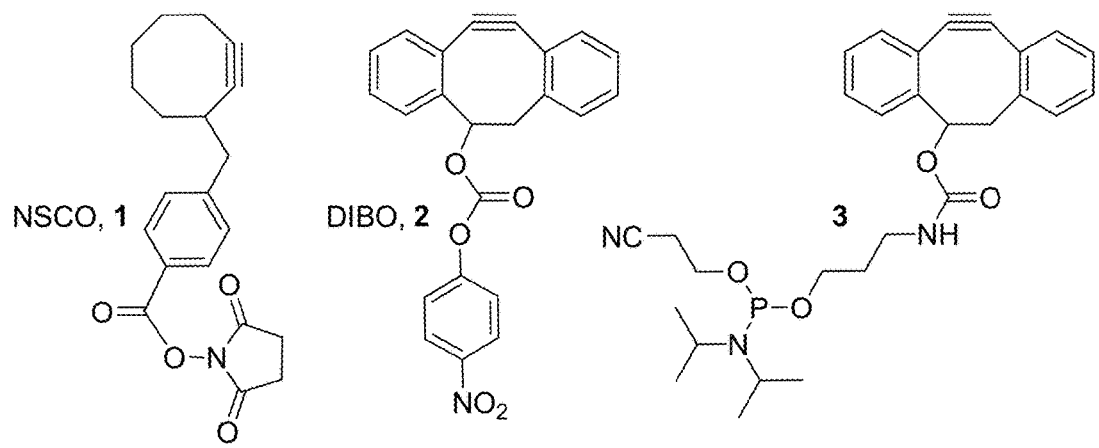
FIG. 4 shows (NSCO, 1 and DIBO, 2) activated cyclooctyne carboxylic acids for labelling amino-modified oligonucleotides and (3) DIBO phosphoramidite for insertion during solid-phase oligonucleotide synthesis.

The speed of reaction of various alkynes with azides at low concentration under DNA-templated conditions was investigated. It was investigated whether they would remain unreactive in a non-templated mode. DNA templation accelerates reaction rates by several orders of magnitude. Two activated cyclooctyne derivatives (FIG. 4) were synthesised for conjugation to amino-functionalised oligonucleotides; the non-substituted cyclooctyne (NSCO, 1) and dibenzocyclooctynol (DIBO, 2). For the method to be suitable for the controlled simultaneous ligation of several oligonucleotides it is important that the ligation reaction occurs only in the presence of a complementary DNA template so that only the desired products are formed. Therefore it was necessary to compare reactivity under both templated and non-templated conditions.

Initially both alkynes were attached post-synthetically to the 5'-end of an aminohexyl-labelled oligonucleotide (ODN-1, 2, Table 1). The NHS ester of 6-azidohexanoic acid was added to a 3'-aminoalkyl labelled oligonucleotide to provide the azide oligonucleotide (ODN-3) which has a fluorescein dye at the 5'-end to allow visualisation at low concentrations. HPLC purification was carried out on all oligonucleotides and the products were characterised by mass spectrometry. Templated and non-templated ligation reactions between azide ODN-3 and alkyne ODN-1 and ODN-2 were carried out in the absence of $Cu^I$.

Discrimination Between Fully Matched and Single Base Pair Mismatched Templates

A solution of the template oligonucleotide (fully matched ODN-5 or mismatched ODN-11) and alkyne oligonucleotide ODN-1 (0.2 nmol of each) in 0.2 M NaCl (100 μL) was annealed for 5 min at 45° C., after which the azide oligonucleotide ODN-3 (0.2 nmol) was added. The reaction mixture was left at 45° C. for 5 min before adding 50 μL formamide and loading directly onto a 20% polyacrylamide/7 M urea gel which was electrophoresed at a constant power of 20 W for 3 hr in 0.09 M Tris-borate-EDTA buffer. Identical results were obtained from the SPAAC reaction if the azide oligonucleotide was annealed to the templates and the alkyne oligonucleotide was added subsequently.

Figure 5A:
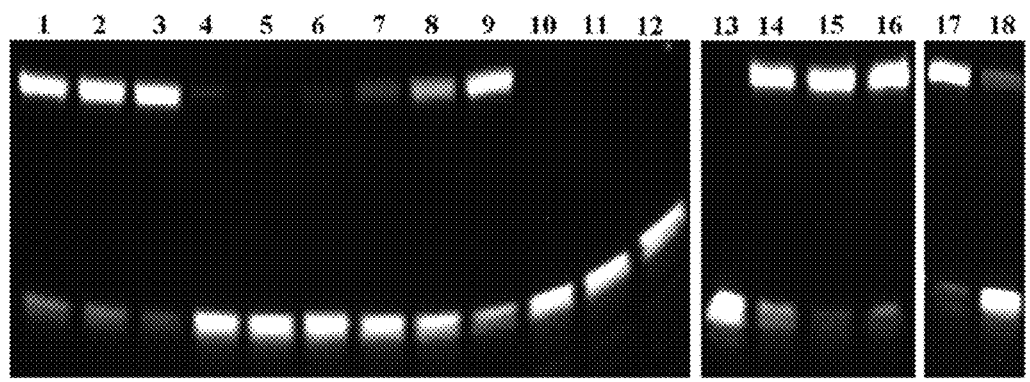
FIG. 5a shows SPAAC templated and non-templated reactions comparing DIBO and NSCO alkyne oligonucleotides.

FIG. 5a shows SPAAC templated and non-templated reactions comparing DIBO and NSCO alkyne oligonucleotides.

Lanes 1-3: templated reactions using DIBO ODN-1; 0 min, 5 min, 30 min, RT, lanes 4-6: non-templated reactions using DIBO ODN-1; 0 min, 5 min, 30 min, RT, lanes 7-9: templated reactions using NSCO ODN-2; 0 min, 5 min, 30 min, RT, lanes 10-12: non-templated reactions using NSCO ODN-2; 0 min, 5 min, 30 min, RT, lane 13: azide ODN-3, lanes 14-16: templated reactions using DIBO ODN-1; 1 min, 3 min, 5 min, RT, lanes 17 and 18 discrimination between fully matched and mismatched templated reactions using DIBO ODN-1 and templates ODN-5, (fully matched, lane 17) and ODN-11 (single base pair mismatch, lane 18); 5 min, 45° C. All reactions performed at 2 μM oligonucleotide conc. in 0.2 M aq. NaCl for the specified time then mixed with formamide and loaded directly onto a 20% polyacrylamide gel.

Of the two cyclooctynes tested, DIBO (2) was much faster in templated ligation (FIG. 5a). This greater reactivity towards azides may be due to additional ring strain and electron withdrawing properties. Reactions with this alkyne proceeded cleanly and were essentially complete within 1 min at 2 μM DNA concentration. NSCO (1) also reacted cleanly but required more than 30 min for complete reaction. In both cases the non-templated reactions gave little or no product under otherwise identical conditions (FIG. 5a). Importantly, introduction of a single mismatch base pair between template ODN-11 and DIBO-labelled ODN-1 was sufficient to inhibit the ligation reaction (FIG. 5a lanes 17, 18), pointing to future applications in genetic analysis.

Figure 5B:
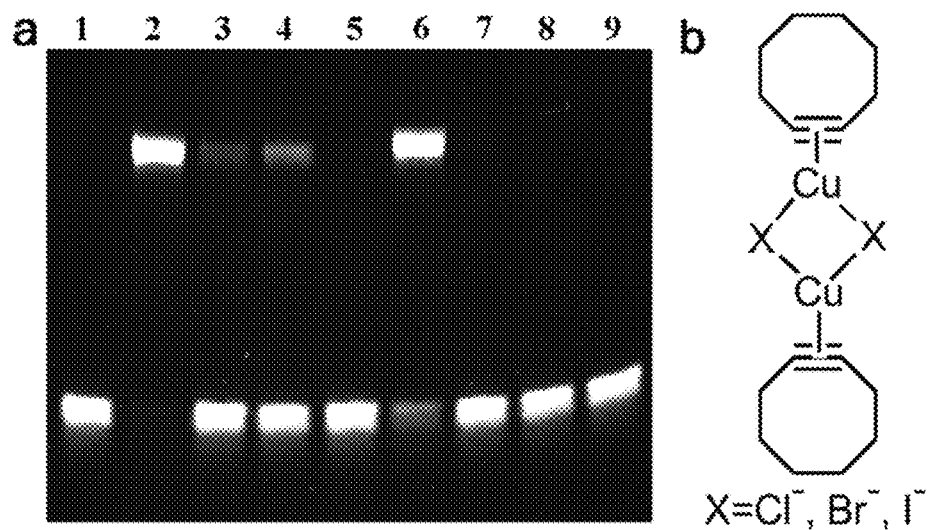
FIG. 5b shows a: SPAAC templated and non-templated reactions using alkyne oligonucleotides pre-treated with $Cu^I$.

The addition of $Cu^I$ strongly inhibited the SPAAC reaction (FIG. 5b(a) lanes 4, 5, 8, 9). FIG. 5b shows a: SPAAC templated and non-templated reactions using alkyne oligonucleotides pre-treated with $Cu^I$. Lane 1: azide ODN-3, lanes 2 and 3: control, templated and non-templated SPAAC reactions using the DIBO alkyne oligonucleotide (ODN-1), lanes 4 and 5: templated and non-templated reactions using DIBO oligonucleotide (ODN-1) pre-treated with $Cu^I$, lanes 6 and 7: control; templated and non-templated SPAAC reactions using the NSCO alkyne oligonucleotide (ODN-2), lanes 8 and 9: templated and non-templated reactions using NSCO oligonucleotide (ODN-2) pre-treated with $Cu^I$. All reactions carried out at 2 μM DNA conc. in 0.2 M NaCl for 30 min at room temperature before loading directly onto a 20% polyacrylamide gel. b: Cu(I)-cyclooctyne complex.

To test the stability of the putative complex with cuprous ion, the alkyne oligonucleotides were treated with Cu$^I$ then all small molecules were removed by sephadex gel-filtration before carrying out the SPAAC reaction. This process did not restore the reactivity of the alkyne suggesting that the alkyne-Cu$^I$ complex survived gel-filtration (FIG. 5b(a)).

Ultraviolet Melting Studies

UV melting experiments were performed on a Varian Cary 4000 Scan UV-Visible spectrophotometer at 1 µM oligonucleotide concentration in 10 mM sodium phosphate with 200 mM NaCl buffer at pH 7.0. The melting temperature (Tm) was calculated at 260 nm using Cary WinUV Thermal application software. The samples were initially denatured by heating to 84° C. at 10° C./min then cooled to 20° C. at 1° C./min-1 and heated to 80° C. at 1° C./min-1. Three successive melting curves were measured and averaged.

Ultraviolet melting studies on duplexes containing the alkynes NSCO (1) and DIBO (2) showed a decrease of ~7° C. in melting temperature (Tm) compared with the unmodified duplex which had a Tm of 66.1° C. The similarity in Tm for both ligated oligonucleotides was expected as both triazole linkers are quite long. If the linker was short there might be a difference in stability between duplexes containing the two different alkynes as DIBO is more bulky, and might also participate in aromatic stacking interactions with the nucleobases.

To evaluate the effect of the length of cyclooctyne linker on click reactivity, and to investigate the possible synthesis of cyclooctyne oligonucleotides which also contain sensitive fluorescent dyes or other labels which have to be added as active esters after solid-phase synthesis the phosphoramidite derivative 3 of DIBO (FIG. 4) was prepared. The cyclooctyne was completely stable to oligonucleotide synthesis and deprotection conditions, including heating in conc. aqueous ammonia for 1 hr at 55° C. Pure alkyne-labelled oligonucleotides were readily obtained and these gave efficient templated ligation with azide oligonucleotides. UV melting of the duplex containing the ligated product (ODN-8) from phosphoramidite 3 (propylcarbamoyl linker) gave a similar Tm to that obtained from the ligated product (ODN-6) derived from the alkyne active ester (amidohexyl linker).

TABLE 1

| Code | Oligonucleotide sequences |
|---|---|
| ODN-1 | $^{DIBO}$K-GCGATCAATCAGACG |
| ODN-2 | $^C$K-GCGATCAATCAGACG |
| ODN-3 | F-CTTTCCTCCACTGTTGCz |
| ODN-4 | $^{DIBO}$K$_1$-GCGATCAATCAGACG |
| ODN-5 | TTTATTGATCGCGCAACAGTGTTT |
| ODN-6 | F-CTTTCCTCCACTGTTGC<u>X</u>GCGAT CAATCAGACG |
| ODN-7 | F-CTTTCCTCCACTGTTGC<u>Y</u>GCGAT CAATCAGACG |
| ODN-8 | F-CTTTCCTCCACTGTTGC<u>Z</u>GCGAT CAATCAGACG |
| ODN-9 | Fz$^{DIBO}$K$_1$-GCGATCAATCAGACG |
| ODN-10 | CTTTCCTCCACTGTTGCGCGATC AATCAGACG |
| ODN-11 | TTTATTCATCGCGCAACAGTGTTT |

Oligonucleotide sequences. F = fluorescein, z = amino C7 labelled with 6-azidohexanoic acid, $^C$K = aminohexyl labelled with NSCO (1), $^{DIBO}$K = aminohexyl labelled with DIBO (2), $^{DIBO}$K$_1$ = dibenzocyclooctynyl derived from phosphoramidite (3). X, Y and Z = ligated triazole products derived from ODN-3 with ODN-1, ODN-2 and ODN-4 respectively. Fz$^{DIBO}$ = 6-fluoresceinamidopropyl azide + DIBO.

Two cyclooctynes have been incorporated into oligonucleotides and used in SPAAC reactions. Templated DNA ligation was very fast and a single base pair mismatch was sufficient to strongly inhibit the reaction. This approach may be used for multiple simultaneous templated DNA ligation reactions if participating oligonucleotides are attached to either two alkynes or two azides.

The cyclooctyne and azide oligonucleotides are both stable in aqueous buffer. The SPAAC reaction on DNA has potential for applications in biology, genomics and nanotechnology.

Cross Linking of Strands

General:

All reagents used were purchased from Aldrich, Avocado or Fluka and used without purification with the exception of the following solvents, which were purified by distillation in the labs: Toluene, THF (over sodium wire), DCM, DIPEA and pyridine (over calcium hydride). Most the reactions were carried out under an argon atmosphere using oven-dried glassware with purified and distilled solvents, the thin layer chromatography was performed using Merck Kieselgel 60 F24 (0.22 mm thickness, aluminium backed) and the compounds were visualised by irradiation at 254 nm or by a suitable staining system. Column chromatography was carried out under pressure using Fisher scientific DAVISIL 60A (35-70 micron) silica.

$^1$H NMR spectra were measured at 300 MHz on a Bruker AC300 spectrometer or 400 MHz on a Bruker DPX400 spectrometer. $^{13}$C NMR spectra were measured at 75 MHz and 100 MHz on the same spectrometers respectively. Chemical shifts are given in ppm relative to tetramethylsilane, and J values are given in Hz and are correct to within 0.5 Hz. $^{31}$P NMR spectra were recorded on a Bruker AV 300 spectrometer at 121 MHz. All spectra were internally referenced to the appropriate residual undeuterated solvent signal. Assignment was also aided by COSY ($^1$H-$^1$H) and HMQC ($^1$H-$^{13}$C).

Low-resolution mass spectra were recorded using electrospray technique on a Fisons VG platform instrument or a Waters ZMD quadrupole mass spectrometer in acetonitrile or methanol (HPLC grade). High-resolution mass spectra were recorded in acetonitrile or methanol (HPLC grade) using electrospray ionization on a Bruker APEX III FT-ICR mass spectrometer.

Synthesis of DIBO Phosphoramidite Monomer which is Useful for Cross-Linking Polynucleotide Duplexes Across the Minor or Major Groove.

The scheme below shows the synthesis of the 2'-DIBO-5-methyluridine phosphoramidite compound B: (i) diphenyl carbonate, NaHCO$_3$ cat., 100° C., DMF, 90%, (ii) DMTCl, pyridine, rt, 89%, (iii) ethylene glycol, Ti(O$^i$Pr)$_4$, NaHCO$_3$ cat., THF, 150° C., 79%, (iv) MsCl, Et$_3$N, DCM, 57%, (v) NaN$_3$, DMF, 18-crown-6, 89%, (vi) Ph$_3$P, H$_2$O, THF, 89% (vii) DCM, Et$_3$N, 88%, (viii) ($^i$Pr)$^2$NP(Cl)OCH$_2$CH$_2$CN, DIPEA, DCM, rt, 59.4%.

25
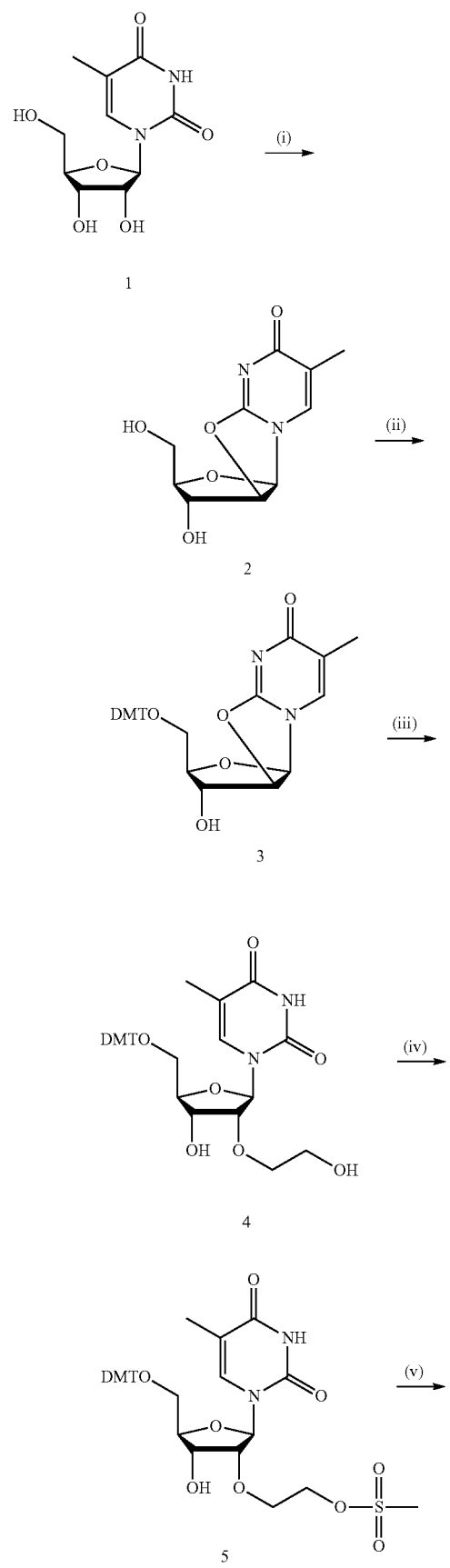
26
-continued
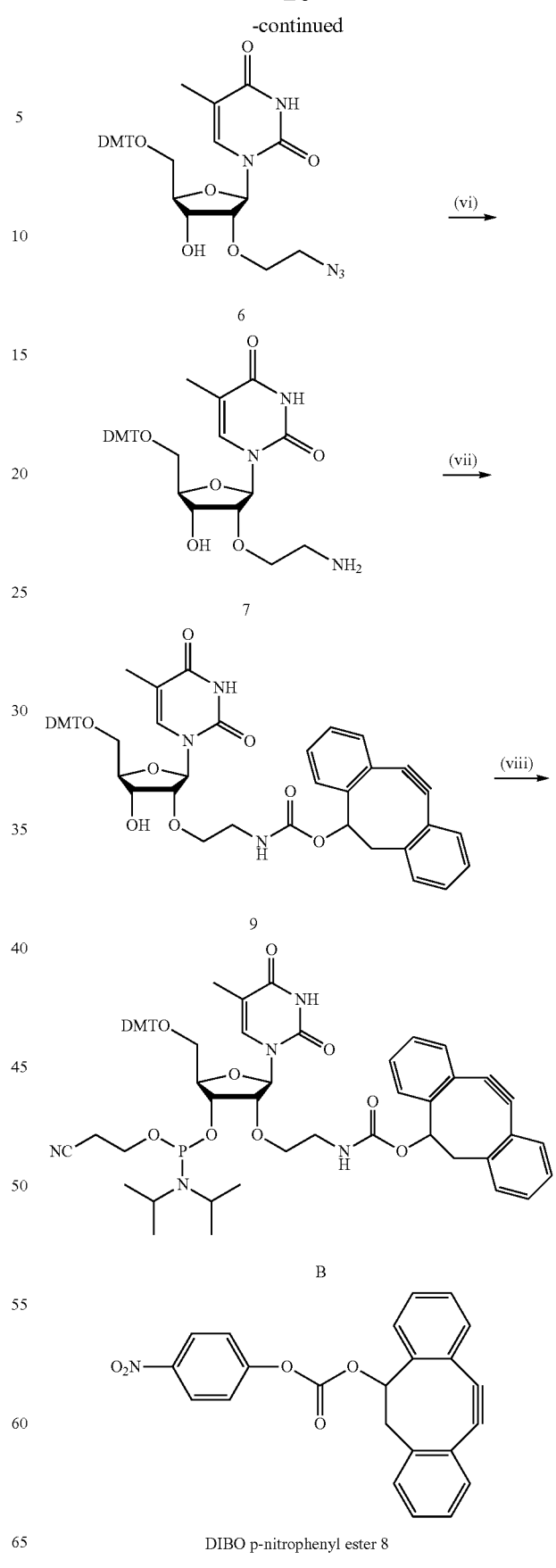

The coupling of the DIBO active ester to compound 7 was completed in 88% yield, the next step was to phosphitylate compound 9 to give the 2'-DIBO-5-methyluridine phosphoramidite compound B in 59.4% yield.

Numbering System

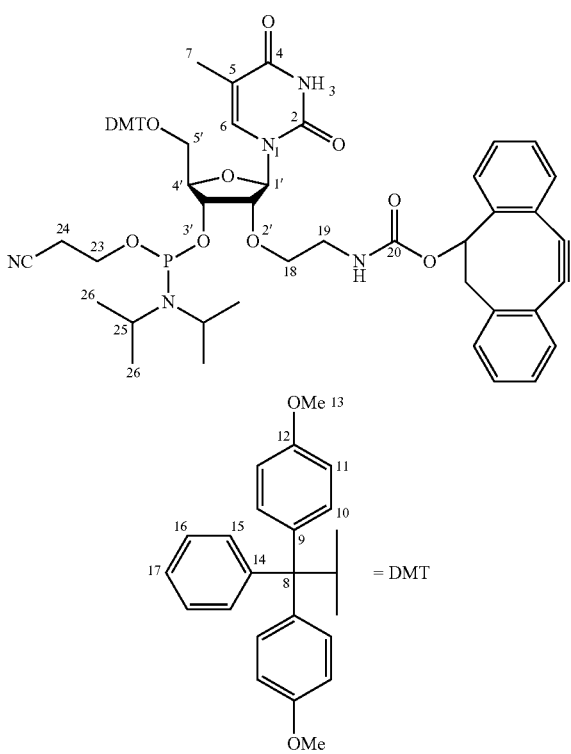

2'-O-{2-[3-(7,8-Didehydro-1,2:5,6-dibenzocyclooctynyl)oxyamido]ethyl}-5'-O-(4,4'-dimethoxytrityl)-5-methyluridine (9)

To a solution of DIBO p-nitrophenyl ester 8 (0.75 g, 1.93 mmol) in anhydrous DCM (14 mL) was added anhydrous Et$_3$N (1.5 mL) followed by compound 7 (1.4 g, 2.32 mmol) under an argon atmosphere at room temperature. The reaction mixture was stirred for 5 hrs 15 min at room temperature, it was then diluted with DCM (10 mL) and the resulting mixture was extracted with saturated brine (2×50 mL). The combined extracts were dried over Na$_2$SO$_4$, and the solvent was removed in vacuo. The crude product was purified by column chromatography (60-100% EtOAc/Hexane) to give compound 9 as a white foam (1.43 g, 1.69 mmol, 88%). R$_f$ 0.45 (10% MeOH/DCM).

$^1$H NMR (400 MHz, CDCl$_3$) δ 9.60 (br. s., 1H, NH), 7.69-7.65 (m, 1H, H6), 7.49-7.44 (m, 1H, ArH), 7.40 (d, 2H, J=7.6 Hz, ArH), 7.36-7.17 (m, 16H, ArH), 6.82 (d, 4H, J=8.6 Hz, H$^{11}$), 5.97 (d, 1H, J=2.0 Hz, H$^{1'}$) 5.75 (br. s., 1H, NH), 5.48 (br. s., 1H, H$^{21}$), 4.48-4.39 (m, 1H, H$^{3'}$), 4.07-3.98 (m, 2H, H$^{2'}$+H$^{4'}$), 3.94 (br. s., 1H, H$^{18/H19}$), 3.82 (br. s., 1H, H$^{18/H19}$), 3.57-3.45 (m, 2H, H$^{5'}$+H18/H19), 3.77 (s, 6H, 2×OCH$_3$), 3.44-3.34 (m, 2H, H$^{5'}$+H$^{18}$/H$^{19}$), 3.14 (app. d, 1H, J=14.7 Hz, H$^{22}$), 2.86 (dd, 1H, J=16.1, 2.5 Hz, H$^{22}$), 1.38 (d, 3H, J=1.0 Hz, H$^7$ (CH$_3$)) ppm $^{13}$C NMR (101 MHz, CDCl$_3$) δ164.2 (C4), 159.0 (C12), 156.2 (C20), 151.2 (CAr), 151.0 (C2), 144.6 (CAr), 135.7 (C9), 135.6 (CAr), 135.4 (C6), 130.4 (CHAr), 130.2 (CHAr), 128.4 (CHAr), 128.3 (CHAr), 128.2 (CHAr), 127.4 (CHAr), 127.3 (CHAr), 126.5 (CHAr), 126.2 (CHAr), 124.0 (CHAr), 121.6 (CAr), 116.0 (CHAr), 113.6 (H11), 113.2 (CAr), 111.5 (CAr), 110.2 (CAr), 88.1 (C1'), 87.1 (C8), 83.6 (C2'), 83.1 (C4'), 70.7 (C18/H19), 69.2 (C3'), 62.1 (C5'), 55.5 (2×OMe), 46.5 (C22), 41.2 (C18/C19), 12.2 (CH$_3$) ppm LRMS [ES$^+$, MeOH]: m/z (%): 872.5 ([M+Na]$^+$, 75%).
HRMS [ES$^+$]: C$_{50}$H$_{47}$N$_3$NaO$_{10}$ requires 872.3154 found 872.3155.

2'-O-{2-[3-(7,8-Didehydro-1,2:5,6-dibenzocyclooctynyl)oxyamido]ethyl}-5'-O-(4,4'-dimethoxytrityl)-5-methyluridine 3'-O-(2-cyanoethyl-N,N-diisopropyl)phosphoramidite (B)

B

To a solution of compound 9 (0.35 g, 0.42 mmol) in distilled DCM (5 mL) and distilled DIPEA (0.15 mL, 0.83 mmol), strictly under an argon atmosphere and excluding moisture, was added chloro-phosphitylating reagent (0.13 mL, 0.58 mmol) dropwise, and the reaction was stirred at rt for 3 hours. The reaction mixture was transferred to a separating funnel containing distilled DCM (25 mL), and washed with saturated aq KCl (25 mL) then transferred under argon and concentrated in vacuo. Purification by column chromatography (60% EtOAc/hexane, 0.5% pyridine) under argon pressure, gave the desired product, compound B as a diastereomeric mixture (ca. 1:1:1:1), as an air-sensitive white foam (0.26 g, 0.25 mmol, 59.4%). M$_w$=1050.14, C$_{59}$H$_{64}$N$_5$O$_{11}$P, R$_f$ 0.26 (55% EtOAc/Hexane)

$^{31}$P NMR (121 MHz, CD$_3$CN) δ 150.86, 150.79, 149.98, 149.82 (isomers)

$^1$H NMR (400 MHz, CD$_3$CN) δ 9.20 (br. s., 1H, NH) 7.60-7.53 (m, 2H, ArH), 7.51-7.22 (m, 18H, ArH), 6.87 (dd,

4H, J=8.3, 5.3 Hz, H11), 6.09 (br. s., 1H, NH), 5.94 (d, 1H, J=9.6 Hz, H$^{1'}$), 5.36 (br. s., 1H, H$^{21}$), 4.59-4.41 (m, 1H, H$^{3'}$), 4.25-4.13 (m, 2H, H$^{2'}$+H$^{4'}$), 3.91-3.78 (2×m, 1H, H$^{23}$), 3.77-3.71 (m, 8H, 2×OMe+H$^{18/19}$), 3.70-3.59 (2×m, 1H, H$^{23}$), 3.58-3.54 (m, 2H, H$^{25}$), 3.51-3.41 (m, 1H, H$^{18/19}$), 3.39-3.26 (m, 3H, H$^{5'}$+H$^{19/18}$), 3.17 (d, 1H, J=15.2 Hz, H$^{22}$), 2.82 (d, 1H, J=14.7 Hz, H$^{22}$), 2.64 (br. t, 1H, J=5.8 Hz, H$^{24}$), 2.49 (t, 1H, J=5.8 Hz, H$^{24}$), 1.41, 1.39, 1.38 and 1.37 (s, 3H, CH$_3$), 1.18-1.11 (m, 9H, H$^{26}$), 1.03 (dd, 3H, J=6.6, 3.5 Hz, H$^{26}$) ppm LRMS: [ES$^+$, MeCN] m/z (%) 1072.9 ([M+Na]$^+$, 100%)

Synthesis of Compound C, which is Useful for Cross-Linking Polynucleotide Duplexes Across the Major Groove.

The scheme below shows the synthesis of 5-DIBO functionalised-dT phosphoramidite compound C: (i) DMTCl, pyridine, RT, 4 hr, 82% (ii) Propargylamine, Cu$^I$, Pd(PPh$_3$)$_4$, Et$_3$N, DMF, 2 hr 45 min, RT, 79% (iii) DCM, Et$_3$N, 3 hr 45 min, 55° C., 73% (iv) ($^i$Pr)$_2$NP(Cl)OCH$_2$CH$_2$CN, DIPEA, DCM, 1 hr, RT, 72%.

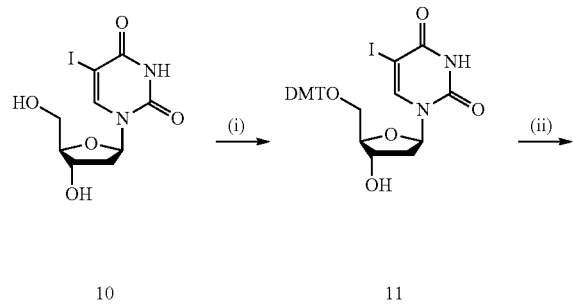

10   11

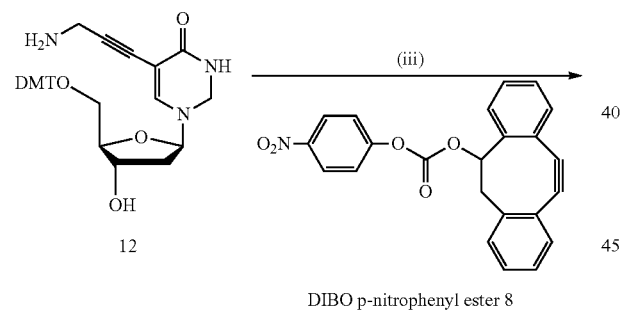

12

DIBO p-nitrophenyl ester 8

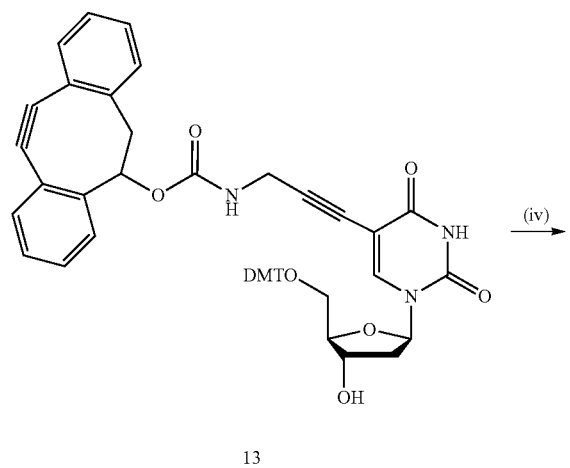

13

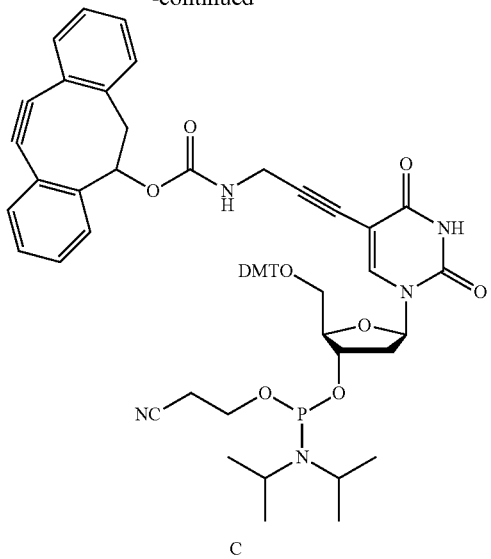

C

Compound C has been synthesised and all the steps gave good yields. The first step was tritylation of 5-iodo-2'-deoxyuridine (5-iodo-dU) (10). The subsequent palladium cross-coupling reaction of compound 11 with propargylamine gave intermediate compound 12. DIBO p-nitrophenyl ester was coupled to compound 12 to give compound 13, which was phosphitylated to yield the DIBO-dT phosphoramidite compound C.

5'-O-(4,4'-Dimethoxytrityl)-5-iodo-2'-deoxyuridine (11)

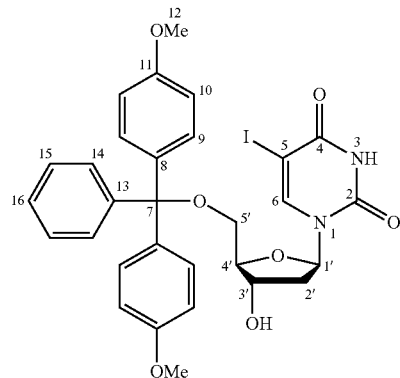

5-iodo-2'-deoxyuridine (10) (5.5 g, 15.5 mmol) was co-evaporated with distilled pyridine (3×10 mL) and suspended in distilled pyridine (40 mL). To this was added dropwise a solution of DMTCl (6.31 g, 18.6 mmol) in distilled pyridine (35 mL) over a period of 40 minutes and the reaction was stirred at rt for 4 hrs 15 mins. The reaction was quenched by the addition of MeOH (40 mL) and was stirred for 20 minutes. The reaction volume was reduced by two thirds in vacuo, diluted with DCM (200 mL) and washed with H$_2$O (200 mL) and NaHCO$_3$ (200 mL). Following purification by column chromatography using a gradient of 0% to 5% MeOH in DCM with 0.5% pyridine, the product, compound 11 was afforded as a foam (8.35 g, 12.7, 82%). R$_f$ 0.44 (10% MeOH/DCM).

$^1$H NMR (300 MHz, d$_6$-DMSO) δ 11.74 (s, 1H, NH), 8.02 (s, 1H, H$^6$), 7.44-7.11 (m, 13H, ArH), 6.90 (d, 4H, J=8.8 Hz, H$^{10}$), 6.11 (t, 1H, J=6.8 Hz, H$^{1'}$), 5.31 (d, 1H, J=4.4 Hz, OH$^{3'}$), 4.27-4.19 (m, 1H, H$^{3'}$), 3.90 (q, 1H, J=3.8 Hz, H$^{4'}$), 3.74 (s, 6H, H$^{12}$), 3.24-3.13 (m, 2H, H$^{5'}$), 2.28-2.11 (m, 2H, H$^{2'}$) ppm.

$^{13}$C NMR (75 MHz, d$_6$-DMSO) δ 160.5 (C$^2$), 158.1 (C$^4$), 150.0 (CH$^6$), 149.6 (C$^{Ar}$), 144.7 (CH$^{Ar}$), 144.2 (C$^{Ar}$), 136.1 (CN$^{Ar}$), 135.4 (C$^{Ar}$), 135.4 (C$^{Ar}$), 129.7 (CH$^{Ar}$), 127.9 (CH$^{Ar}$), 127.6 (CH$^{Ar}$), 126.7 (CH$^{Ar}$), 123.9 (CH$^{Ar}$), 113.3 (C$^{10}$), 85.8 (C$^4$), 84.9 (C$^{1'}$), 70.5 (C$^{3'}$), 69.8 (C5), 63.7 (C$^{5'}$), 55.0 (C$^{12}$), 39.9 (C$^{2'}$) ppm.

LRMS [ES$^+$, MeOH]: m/z (%): 679.2 ([M+Na]$^+$, 100%).

5-(3-Aminopropynyl)-5'-O-(4,4'-dimethoxytrityl)-2'-deoxyuridine (12)

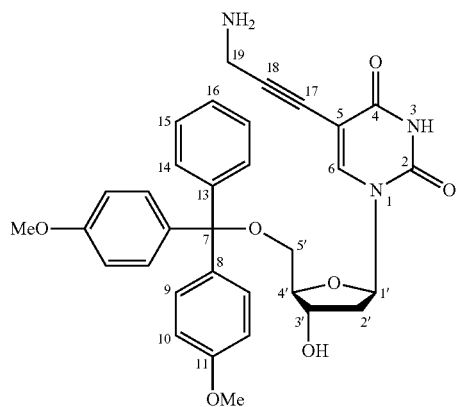

To a mixture of compound 11 (3.0 g, 4.57 mmol) and CuI (0.17 g, 0.91 mmol) in anhydrous DMF (23 mL) under an argon atmosphere, was added propargylamine (0.6 mL, 9.14 mmol) and triethylamine (14 mL). The reaction was stirred for 10 minutes at rt before Pd(PPh$_3$)$_4$ (0.53 g, 0.46 mmol) was added and the reaction stirred at rt for 2 hrs 45 mins. The solvent was removed in vacuo and purification by column chromatography (2-4% MeOH in DCM with 1% pyridine) afforded the product, compound 12 as a pale yellow foam (2.11 g, 3.61 mmol, 79%). R$_f$ 0.31 (10% MeOH/DCM).

$^1$H NMR (400 MHz, d$_6$-DMSO) δ 7.91 (s, 1H, H$^6$), 7.47-7.39 (m, 2H, ArH), 7.36-7.19 (m, 7H, ArH), 6.90 (d, 4H, J=9.1 Hz, H$^{10}$), 6.13 (t, 1H, J=6.8 Hz, H$^{1'}$), 4.33-4.25 (m, 1H, H$^{3'}$), 3.97-3.89 (m, 1H, H$^{4'}$), 3.74 (s, 6H, 2×OCH$_3$), 3.25 (br. dd, 3H, J=10.4, 5.3 Hz, H$^{5'}$+H$^{19}$), 3.12 (dd, 1H, J=10.4, 2.8 Hz, H$^{5'}$), 2.32-2.14 (m, 2H, H$^{2'}$) ppm $^{13}$C NMR (101 MHz, d$_6$-DMSO) δ 161.6 (C$^4$), 158.1 (C$^{11}$), 149.3 (C$^2$), 144.8 (C$^{Ar}$), 142.5 (C$^6$), 135.5 (C$^{Ar}$), 135.3 (C$^{Ar}$), 129.7 (CH$^{Ar}$), 127.9 (CH$^{Ar}$), 127.6 (CH$^{Ar}$), 126.6 (CH$^{Ar}$), 113.2 (O), 98.9 (C$^5$), 85.8 (C$^4$), 84.8 (C$^{1'}$), 70.4 (C$^{3'}$), 63.7 (C$^{5'}$ & C$^{19}$), 55.0 (C$^{12}$), 40.0 (C$^{2'}$) ppm.

LRMS [ES$^+$, MeOH]: m/z (%): 606.4 ([M+Na]$^+$, 100%).

5-{3-[3-(7,8-didehydro-1,2:5,6-dibenzocyclooctynyl)oxyamido]propynyl}-5'-O-(4,4'-dimethoxytrityl)-2'-deoxyuridine (13)

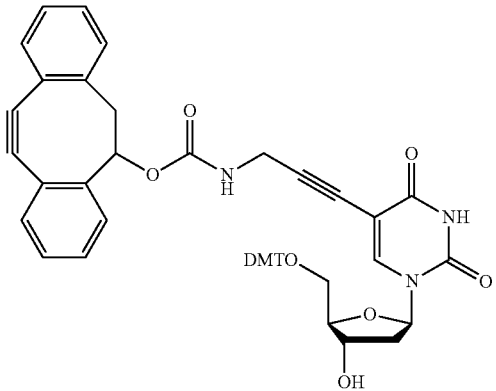

To a solution of DIBO p-nitrophenyl ester (1.42 g, 3.68 mmol) in anhydrous DCM (25 mL) was added anhydrous Et$_3$N (2.4 mL) followed by compound 12 (1.79 g, 3.07 mmol) under an argon atmosphere. The reaction mixture was stirred for 3 hrs 45 min at 55° C., it was then diluted with DCM (250 mL) and the resulting mixture was extracted with saturated brine (2×250 mL). The combined extracts were dried over Na$_2$SO$_4$, and the solvent was removed in vacuo. The crude product was purified by column chromatography (60-100% EtOAc in Hexane) to give compound 13 as a white foam (1.85 g, 2.23 mmol, 73%). R$_f$ 0.47 (10% MeOH/DCM).

$^1$H NMR (400 MHz, CDCl$_3$) δ 9.71 (br. s., 1H, NH), 8.15 (s, 1H, ArH), 7.36-7.44 (m, 2H, ArH), 7.16-7.34 (m, 14H, ArH), 6.82 (d, 4H, J=8.6 Hz, H$^{10}$), 6.32 (t, 1H, J=6.6 Hz, H$^{1'}$), 5.43 (br. s., 1H, CH$^{DIBO}$), 5.24 (br. s., 1H, NH), 4.56 (d, 1H, J=2.0 Hz, H$^{3'}$), 4.06-4.15 (m, 1H, H$^{4'}$), 3.79-3.87 (m, 2H, H$^{19}$), 3.72 (s, 6H, 2×OCH$_3$), 3.35 (br. s., 2H, H$^{5'}$), 3.10 (d, 1H, J=14.7 Hz, CH$^{DIBO}$), 2.80-2.90 (m, 1H, CH$^{DIBO}$), 2.47-2.57 (m, 1H, H$^{2'}$), 2.23-2.34 (m, 1H, H$^{2'}$) ppm 5-{3-[3-(7,8-didehydro-1,2:5,6-dibenzocyclooctynyl)oxyamido]propynyl}-5'-O-(4,4'-dimethoxytrityl)-2'-deoxyuridine-3'-O-(2-cyanoethyl-N,N-diisopropyl)phosphoramidite (C)

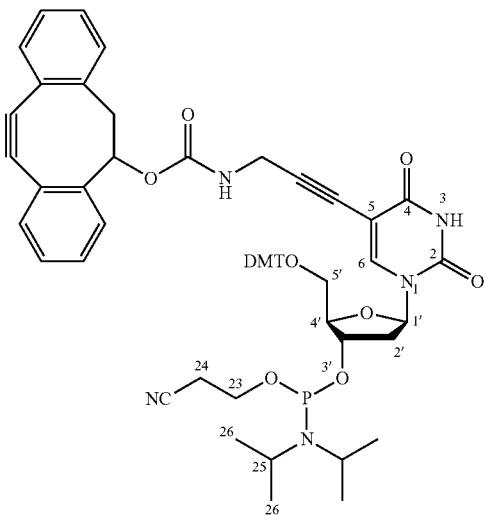

-continued

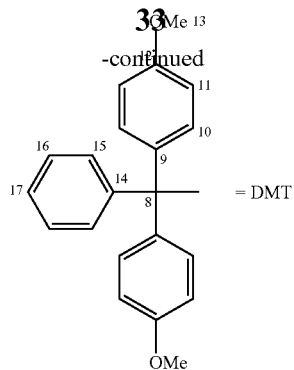

= DMT

To a solution of compound 13 (1.75 g, 2.11 mmol) in distilled DCM (20 mL) and distilled DIPEA (0.73 mL, 4.21 mmol), strictly under an argon atmosphere and excluding moisture, was added chloro-phosphitylating reagent (0.66 mL, 2.95 mmol) dropwise, and the reaction was stirred at rt for 1 hr. The reaction mixture was transferred to a separating funnel containing distilled DCM (60 mL), and washed with saturated aq KCl (70 mL). The organic layer was dried over anhydrous $Na_2SO_4$. The solvent was then removed. Purification by column chromatography (65% EtOAc/hexane, 0.5% pyridine) under argon pressure, gave the desired product, compound C as a diastereomeric mixture, as an air-sensitive white foam (1.57 g, 1.52 mmol, 72%). $M_w$=1030.11, $C_{59}H_{60}N_5O_{10}P$, $R_f$ 0.32 (60% EtOAc/Hexane).

$^{31}P$ NMR (121 MHz, $CD_3CN$) δ 149.26

$^1H$ NMR (400 MHz, $CD_3CN$) δ 9.17 (br. s., 1H, NH), 7.95 (br. d, 1H, J=11.6 Hz, ArH), 7.56-7.43 (m, 3H, ArH), 7.41-7.19 (m, 14H, ArH), 6.91-6.83 (m, 4H, $H^{10}$), 6.17-6.08 (m, 1H, $H^{1'}$), 5.94 (br. s., 1H, NH), 5.36 (br. s., 1H, $H^{21}$), 4.72-4.58 (m, 1H, $H^{3'}$), 4.16 and 4.12 (dd, 1H, J=6.6, 3.0 Hz and J=6.1, 3.5 Hz, $H^{4'}$), 3.87-3.80 (m, 2H, $H^{19}$), 3.79-3.65 (m, 8H, $2 \times OCH_3$ and $H^{23}$), 3.65-3.52 (m, 2H, $H^{25}$), 3.41-3.31 (m, 1H, $H^{5'}$), 3.24 and 3.21 (dd, 1H, J=11.1, 2.5 Hz and J=10.6, 2.5, H5'), 3.17-3.11 (m, 1H, $H^{22}$), 2.82 (dt, 1H, J=15.0, 3.9 Hz, H22), 2.64 (t, 1H, J=6.1 Hz, $H^{24}$), 2.54 (t, 1H, J=6.1 Hz, $H^{24}$), 2.51-2.32 (m, 2H, $H^{2'}$), 1.18-1.14 (m, 9H, $H^{26}$), 1.08 (d, 3H, J=6.6 Hz, $H^{26}$) ppm LRMS [$ES^+$, MeCN]: m/z (%): 1052.7 ([M+Na]$^+$, 100%).

Cross-Linking Reactions

Figure 7:
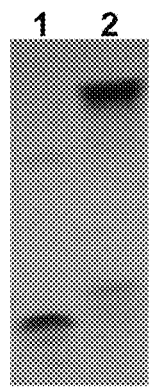
FIG. 7 shows 20% polyacrylamide gel electrophoresis to analyse the non-copper click ligation between complementary DIBO and azide oligonucleotides.

Phosphoramidite compounds B and C (also shown in FIG. 6) were synthesised and attached to oligonucleotides as described above to allow the addition of the dibenzocyclooctynes (DIBO) functionality inside oligonucleotide sequences away from the 5' or 3'-end. Compounds B and C can alternatively be attached at the 5' end of an oligonucleotide or at the 3' end if a universal support is used in solid-phase synthesis. When incorporated into DNA duplexes, compound B has the DIBO in the minor/major groove, and compound C has DIBO in the major groove. The oligonucleotides with DIBO attached were annealed to complementary oligonucleotides that had been attached to azides D, E and F (FIG. 6). When the two complementary oligonucleotides annealed this lead the attached strained alkyne and azide groups to undergo a SPAAC reaction and to the chemical cross-linking of the two complementary DNA strands across the major groove (C+F), across the minor groove (B+D, B+E) or between major or minor grooves (C+D, C+E, B+F). All the above combinations have been shown to work efficiently, and one example is shown in FIG. 7. In the examples examined, the azide-labelled or DIBO-labelled thymidine nucleosides are in opposite strands on adjacent A.T Watson-Crick base pairs. They could also be placed on mismatched base pairs, on other nucleosides other than thymidine, on chemically modified nucleosides, or on nucleoside analogues (examples are given below). If the length of the linkers attaching the DIBO and azide moieties to the nucleoside is increased, bases that are widely separated in the DNA duplex could be joined together. The cross-strand DIBO triazole linkages formed by the click reaction could prevent other molecules from binding to the DNA duplex in the region of the linkers. As such, the linkages could be considered as DNA major groove, minor groove or DNA sequence protecting groups. It is possible (for example) that such protection could prevent DNA from being digested by restriction enzymes, or from being cleaved by minor groove cutters such as DNase-1.

Templated DIBO-Azide Complementary Oligonucleotide Ligation Reactions (Templated SPAAC Reaction)

A solution of the complementary alkyne and azide oligonucleotides (2 nmol of each) in 0.2 M NaCl (100 μL) was left at room temperature for 30 min at RT before adding 50 μL formamide and loading directly onto a 20% polyacrylamide/7 M urea gel. It was electrophoresed at a constant power of 20 W for 3 hr in 0.09 M Tris-borate-EDTA buffer. The gel-purified product was analysed and characterised by mass spectrometry.

Oligonucleotide Sequences:

Res 2334 (Code: RES2334):
5'-ACAGAAZTCATATT where Z = 2'-azidoethoxy-T

Res 2333 (Code: RES2333):
5'-AATATGAAKTCTGT where K = 5-propargyl DIBO dT

Example of DNA Strand Cross-Linking Using Complementary Oligonucleotides Containing DIBO dT and Azide dT In the example of cross linking of complementary DNA strands shown in FIG. 7. FIG. 7 shows 20% polyacrylamide gel electrophoresis to analyse the non-copper click cross-linking between complementary DIBO and azide oligonucleotides: Lane 1; control azide oligonucleotide (Res2334, 2'-azido ethoxy-T). Lane 2; crude reaction mixture of Res2334 and Res2333 (5-propargyl DIBO dT), 20 μM of each DNA strand, 30 min at RT.

Oligonucleotide Sequences:

Res 2334 (Code: RES2334):
5'-ACAGAAZTCATATT where Z = 2'-azidoethoxy-T

Res 2333 (Code: RES2333):
5'-AATATGAAKTCTGT where K = 5-propargyl DIBO dT

The reaction was complete within 5 min.

The click DNA joining chemistry described here may be carried out on solid phase. This may provide a means of controlling the chemistry of multiple oligonucleotide ligation. Oligonucleotides may be added sequentially (in excess) to build long DNA strands, and after each oligonucleotide addition the excess oligonucleotide may be washed away before the next one is added.

Further examples of DIBO alkynes and azide compounds that may be attached to oligonucleotides for use in SPAAC reactions to link oligonucleotides according to the present invention are described below.

Other Examples of DIBO Alkynes
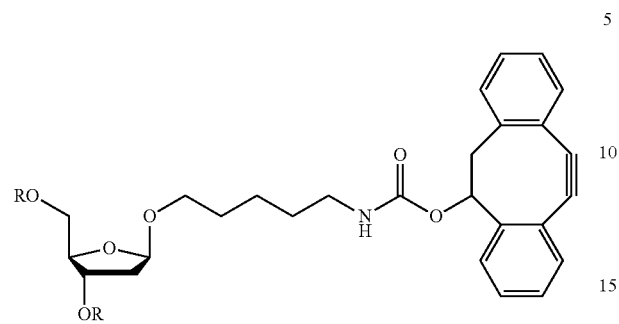
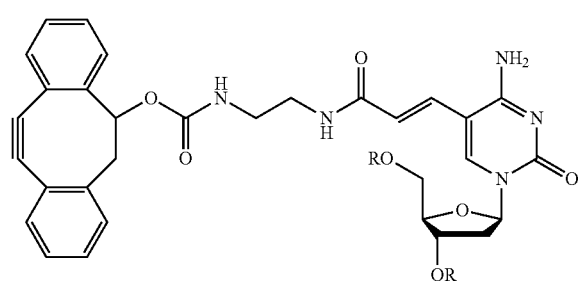
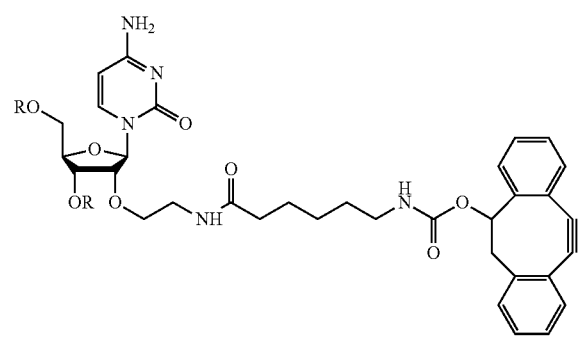
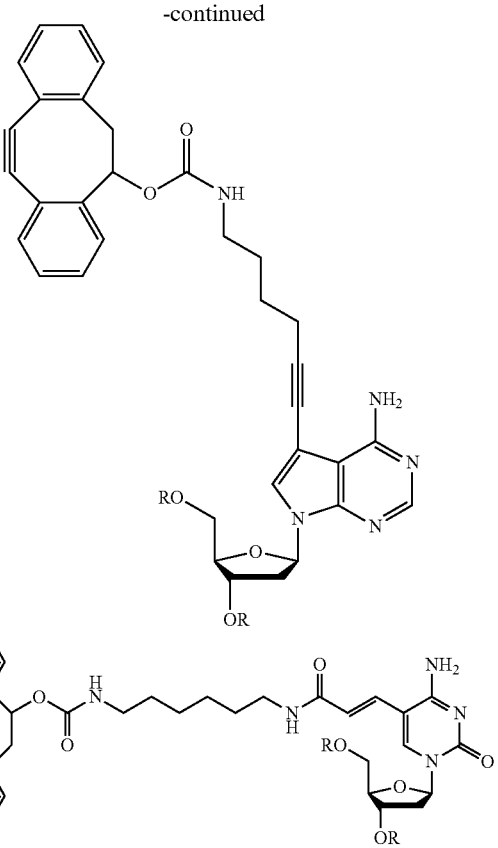
sugars can be deoxyribose, ribose or sugar analogues
RO = rest of oligonucleotide strand
Other Examples of Azides
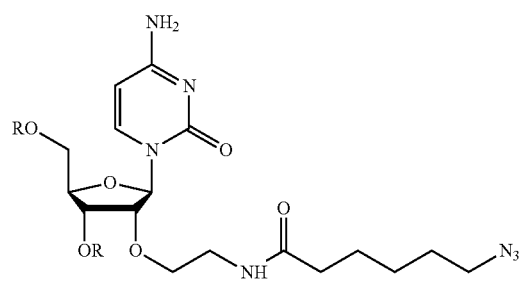
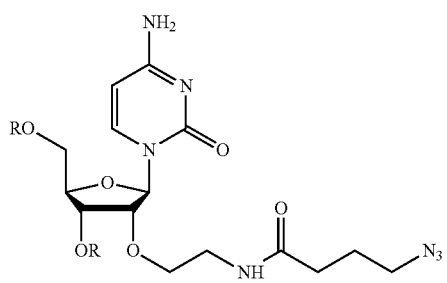

-continued

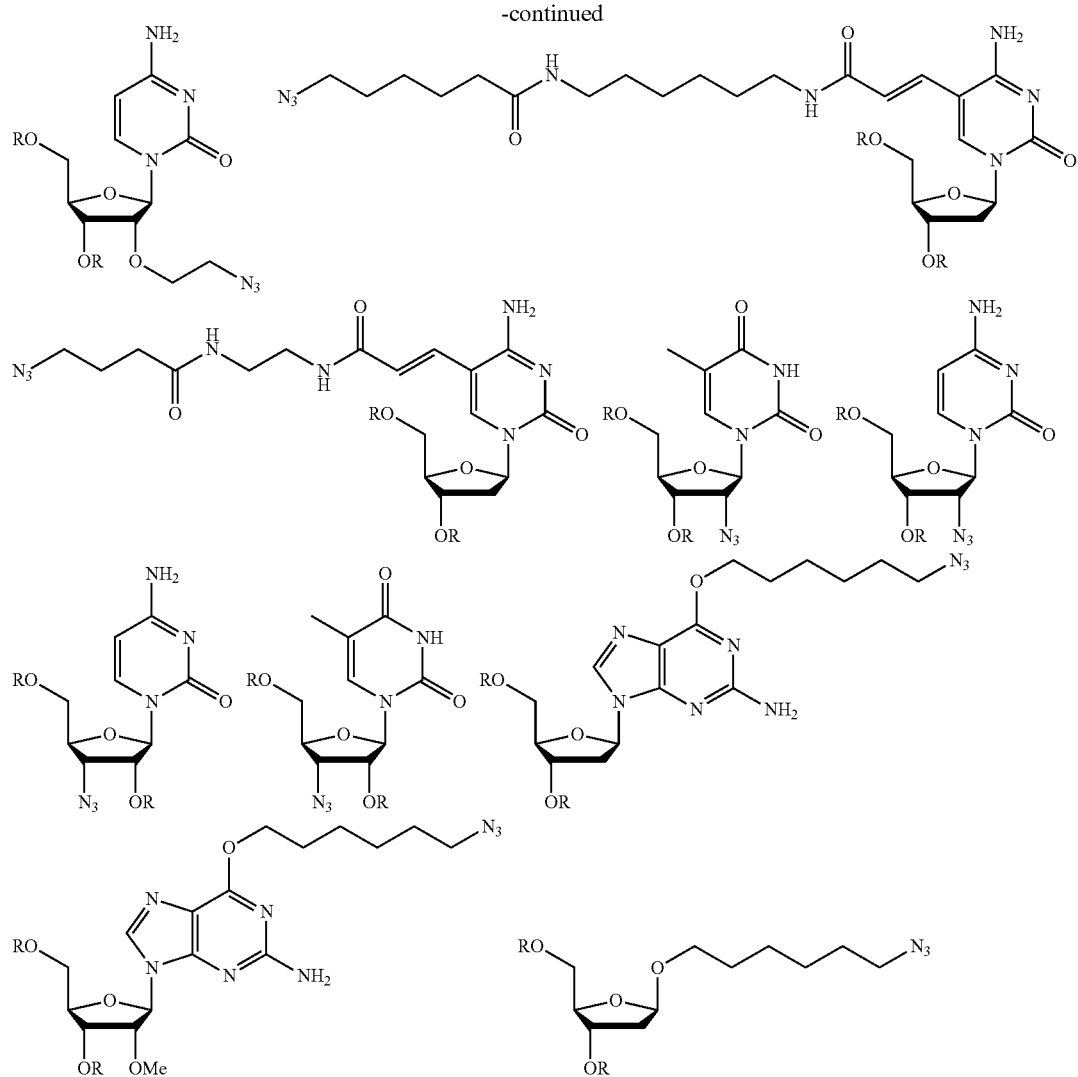

sugars can be deoxyribose, ribose or sugar analogues
RO = rest of oligonucleotide strand

What is claimed is:

1. A method for linking oligonucleotides end-to-end by click reaction, said method comprising:
reacting, by ring strain-promoted click reaction, a ring-strained alkyne group linked to a first oligonucleotide with an azide group linked to a second oligonucleotide to form a triazole linkage between the first and second oligonucleotides, wherein the ring strained alkyne group is linked to a first end of the first oligonucleotide and the azide group is linked to a first end of the second oligonucleotide such that the oligonucleotides are joined end to end,
wherein the click reaction of the first and second oligonucleotides is carried out in copper-free conditions.

2. A method according to claim 1, further comprising: wherein, in addition to the copper-free conditions; the click reaction of oligonucleotides is carried out in metal ion free conditions.

3. A method according to claim 1, wherein the ring-strained alkyne group is linked to the 5' end of the first oligonucleotide.

4. A method according to claim 1, wherein the ring-strained alkyne group is linked to the 3' end of the first oligonucleotide.

5. A method according, to claim 1, the method further comprising at least one of:
a second ring-strained alkyne group linked to a second end of the first oligonucleotide, and
a second azide group linked to a second end of the second oligonucleotide.

6. A method according to claim 5, further comprising:
joining a third oligonucleotide to the first oligonucleotide and/or the second oligonucleotide by click reaction:
reacting an azide group linked to an end of the third oligonucleotide with the second ring-strained alkyne group linked to the first olignucleotide to form a second trizole linkage; or
reacting a ring-strained alkyne group linked to an end of the third oligonucleotide with the second azide group linked to the second olignucleotide to form a second trizole linkage.

7. A method according to claim 1, further comprising: wherein an oligonucleotide portion of the first and second oligonucleotides are selected from the group consisting of DNA, RNA, modified DNA, modified RNA, nucleic acid analogues, and combinations thereof.

8. A method according to claim 1, further comprising: wherein the end to end joining of oligonucleotides is template-mediated.

9. A method according to claim 1, further comprising: wherein the first and second oligonucleotides are orientated by hybridization with a complementary polynucleotide strand before the ring-strained alkyne group and the azide group are joined together.

10. A method according to claim 1, further comprising: wherein the first oligonucleotide is double stranded, and the ring-strained alkyne group is linked to the first oligonucleotide away from an end of the oligonucleotide orientated towards a major groove or a minor groove.

11. A method according to claim 1, further comprising: wherein said ring-strained alkyne group is part of a substituted or un-substituted 7 to 9 membered ring.

12. A method according to claim 11, further comprising: wherein the ring-strained alkyne group is part of a substituted or un-substituted cyclooctyne.

13. A method according to claim 11, further comprising: wherein said ring-strained alkyne group is a dibenzocyclooctyne (DIBO) group.

14. A method according to claim 1, further comprising: wherein the ring-strained alkyne group is a cyclic compound comprising a heteroatom in the ring.

15. A method according to claim 1, further comprising a solid phase, wherein one of the oligonucleotides is attached to the solid phase.

16. A method according to claim 1, further comprising a reporter group selected from the group consisting of fluorescent dyes, biotin, and combinations thereof, wherein at least one of the first, and second oligonucleotides is labeled internally with the reporter group.

17. A method according to claim 1, further comprising a member selected from the group consisting of a nanoparticle, a protein, a biomolecule, and combinations thereof, wherein each oligonucleotide is attached to the member, such that the nanoparticles, proteins, biomolecules, or combinations thereof are linked together as a result of joining the oligonucleotides.

18. A method of claim 1, wherein the first oligonucleotide is linked to a single ring-strained alkyne group, and wherein the second oligonucleotide is linked to a single azide group.

19. An oligonucleotide modified by being linked to a ring-strained alkyne group having a general formula:

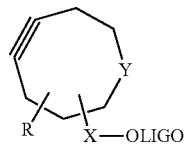

wherein "OLIGO" is the oligonucleotide, X is a linker that attaches the ring-strained alkyne group to the oligonucleotide, Y is carbon or a heteroatom, and R is an optional substituent to the ring or electron withdrawing group.

20. A method for cross-linking oligonucleotide portions by click reaction, said method comprising:
reacting, by click reaction, a ring-strained alkyne group linked to a first oligonucleotide portion with an azide group linked to a second oligonucleotide portion to form a triazole linkage linking the first and second oligonucleotide portions, wherein the click reaction of the first and second oligonucleotide portions is carried out in copper-free conditions, and wherein the two oligonucleotide portions are linked across a duplex by triazole linkage formation between the two strands of the duplex.

21. A method according to claim 20, further comprising: wherein the triazole linkage is formed in a major groove or a minor groove of the duplex.

22. A method according to claim 20, further comprising: wherein said ring-strained alkyne group is part of a substituted or un-substituted 7 to 9 membered ring.

23. A method according to claim 22, further comprising: wherein the ring-strained alkyne group is part of a substituted or un-substituted cyclooctyne.

24. A method according to claim 20, further comprising: wherein the ring-strained alkyne group is a cyclic compound comprising a heteroatom in the ring.

25. A method according to claim 24, further comprising: wherein said ring-strained alkyne group is a dibenzocyclooctyne (DIBO) group.

26. A method according to claim 20, wherein the first oligonucleotide portion is a first oligonucleotide and the second oligonucleotide portion is a second, separate oligonucleotide, and wherein the first and second oligonucleotides are cross-linked across the duplex.

27. A method according to claim 20, wherein the first and second oligonucleotide portions are two parts of the same oligonucleotide.

28. A method according to claim 27, further comprising:
annealing the first and second oligonucleotide portions to form the duplex before crosslinking the first and second oligonucleotides across the duplex by the triazole linkage formation.

29. A method of forming triazole linkages between oligonucleotides by click reaction, the method comprising:
reacting, by click reaction, a ring-strained alkyne group linked to an oligonucleotide with an azide group linked to a separate oligonucleotide to form a triazole linkage, wherein the reacting comprises a ring strain-promoted azide alkyne cycloaddition reaction (SPAAC).

30. A method according to claim 29, wherein the ring-strained alkyne group linked to an oligonucleotide has a general formula:

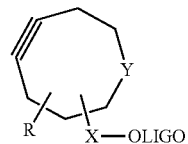

where "OLIGO" is the oligonucleotide, X is a linker that attaches the ring-strained alkyne group to the oligonucleotide, Y is carbon or a heteroatom, and R is an optional substituent to the ring or electron withdrawing group,
wherein the azide group linked to a separate oligonucleotide has the general formula:

OLIGO-N₃ where "OLIGO" is the separate oligonucleotide, and
wherein the ring strain-promoted azide alkyne cycloaddition reaction (SPAAC) is the following mechanism:

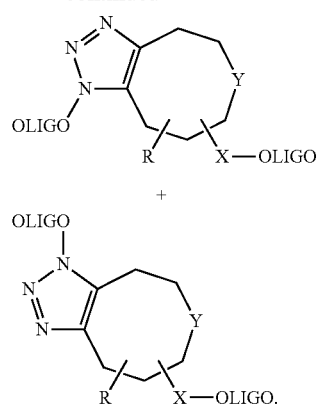

31. A method A method according to claim 30, wherein the ring-strained alkyne group is selected from the following cyclooctyne or dibenzocyclooctyne groups and is linked to the oligionucleotide as shown:

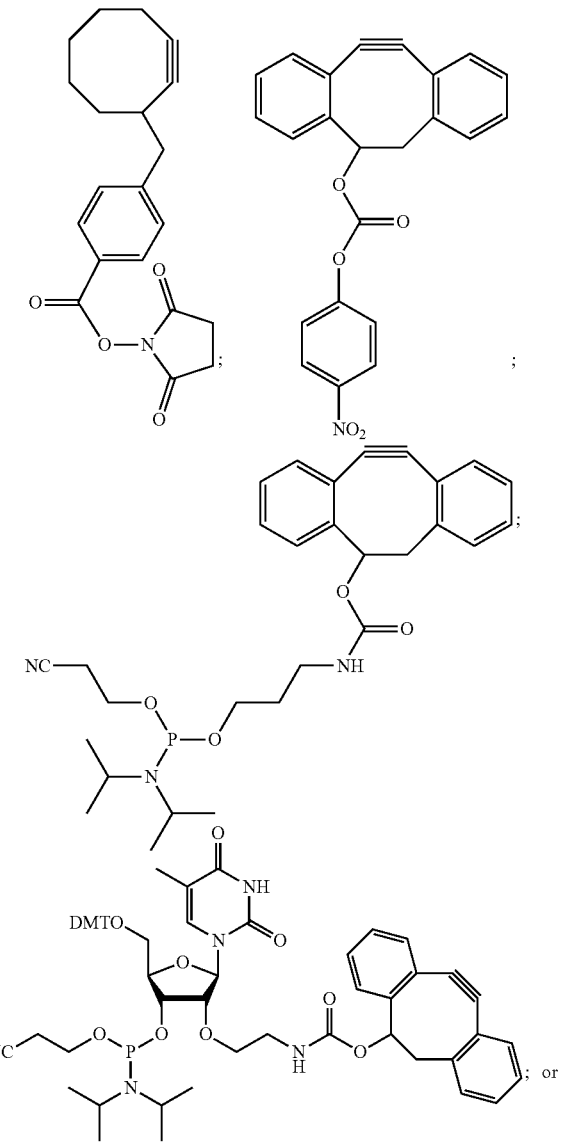

47
-continued
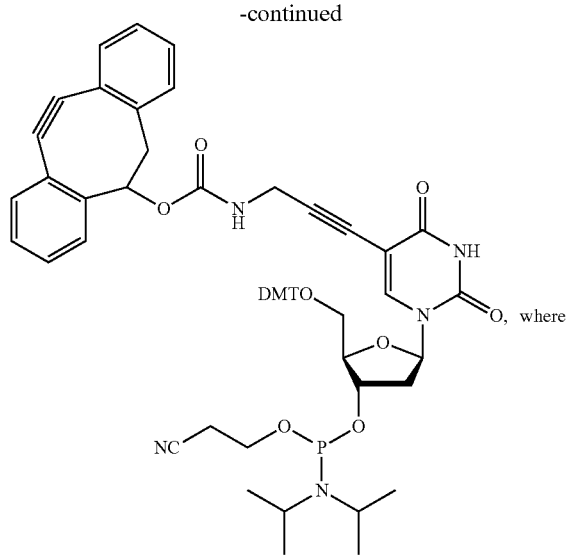
where
48
-continued
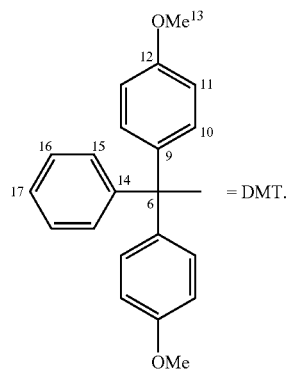
= DMT.
* * * * *

UNITED STATES PATENT AND TRADEMARK OFFICE
CERTIFICATE OF CORRECTION

PATENT NO. : 10,344,047 B2
APPLICATION NO. : 13/409929
DATED : July 9, 2019
INVENTOR(S) : Brown et al.

It is certified that error appears in the above-identified patent and that said Letters Patent is hereby corrected as shown below:

In the Claims

Column 46, Line 19, Claim 31:
Delete the second occurrence of "A method".

Signed and Sealed this
First Day of October, 2019

Andrei Iancu
*Director of the United States Patent and Trademark Office*

SEQUENCE LISTING

<160> NUMBER OF SEQ ID NOS: 13

<210> SEQ ID NO 1
<211> LENGTH: 15
<212> TYPE: DNA
<213> ORGANISM: Artificial Sequence
<220> FEATURE:
<223> OTHER INFORMATION: Oligonucleotide-1 beginning with an aminohexyl
      terminal group labelled with DIBO (2)

<400> SEQUENCE: 1
gcgatcaatc agacg                                                     15

<210> SEQ ID NO 2
<211> LENGTH: 15
<212> TYPE: DNA
<213> ORGANISM: Artificial Sequence
<220> FEATURE:
<223> OTHER INFORMATION: Oligonucleotide-2 beginning with an aminohexyl
      terminal group labelled wtih NSCO (1)

```
<400> SEQUENCE: 2
gcgatcaatc agacg                                                15

<210> SEQ ID NO 3
<211> LENGTH: 17
<212> TYPE: DNA
<213> ORGANISM: Artificial Sequence
<220> FEATURE:
<223> OTHER INFORMATION: Oligonucleotide-3 beginning with a fluorescein
      terminal group and ending with an amino C7 terminal group labelled
      with azidohexanoic acid

<400> SEQUENCE: 3
ctttcctcca ctgttgc                                              17

<210> SEQ ID NO 4
<211> LENGTH: 15
<212> TYPE: DNA
<213> ORGANISM: Artificial Sequence
<220> FEATURE:
<223> OTHER INFORMATION: Oligonucleotide-4 beginning with a
      dibenzocyclooctynyl terminal group derived from phosphoramidite
      (3)

<400> SEQUENCE: 4
gcgatcaatc agacg                                                15

<210> SEQ ID NO 5
<211> LENGTH: 24
<212> TYPE: DNA
<213> ORGANISM: Artificial Sequence
<220> FEATURE:
<223> OTHER INFORMATION: Oligonucleotide-5 is 24-mer that is a template
      oligonucleotide

<400> SEQUENCE: 5
tttattgatc gcgcaacagt gttt                                      24

<210> SEQ ID NO 6
<211> LENGTH: 32
<212> TYPE: DNA
<213> ORGANISM: Artificial Sequence
<220> FEATURE:
<223> OTHER INFORMATION: Oligonucleotide-6 is a ligated product derived
      from ligation of Oligonucleotide-3 (ODN-3) and Oligonucleotide-1
      (ODN-1) via formation of a triazole linkage after nucleotide
      number 17

<400> SEQUENCE: 6
ctttcctcca ctgttgcgcg atcaatcaga cg                             32

<210> SEQ ID NO 7
<211> LENGTH: 32
<212> TYPE: DNA
<213> ORGANISM: Artificial Sequence
<220> FEATURE:
<223> OTHER INFORMATION: Oligonucleotide-7 is a ligated product derived
      from ligation between Oligonucleotide-3 (ODN-3) and
      Oligonucleotide-2 (ODN-2) via formation of a triazole linkage
      after nucleotide number 17

<400> SEQUENCE: 7
ctttcctcca ctgttgcgcg atcaatcaga cg                             32

<210> SEQ ID NO 8
<211> LENGTH: 32
```

```
<212> TYPE: DNA
<213> ORGANISM: Artificial Sequence
<220> FEATURE:
<223> OTHER INFORMATION: Oligonucleotide-8 is a ligated product derived
      from ligation between Oligonucleotide-3 (ODN-3) and
      Oligonucleotide-4 (ODN-4) via formation of a triazole linkage
      after nucleotide number 17

<400> SEQUENCE: 8
ctttcctcca ctgttgcgcg atcaatcaga cg                                      32

<210> SEQ ID NO 9
<211> LENGTH: 15
<212> TYPE: DNA
<213> ORGANISM: Artificial Sequence
<220> FEATURE:
<223> OTHER INFORMATION: Oligonucleotide-9 beginning with
      6-fluoresceinamidopropyl azide + DIBO terminal group

<400> SEQUENCE: 9
gcgatcaatc agacg                                                         15

<210> SEQ ID NO 10
<211> LENGTH: 32
<212> TYPE: DNA
<213> ORGANISM: Artificial Sequence
<220> FEATURE:
<223> OTHER INFORMATION: Oligonucleotide-10 is a 32-mer

<400> SEQUENCE: 10
ctttcctcca ctgttgcgcg atcaatcaga cg                                      32

<210> SEQ ID NO 11
<211> LENGTH: 24
<212> TYPE: DNA
<213> ORGANISM: Artificial Sequence
<220> FEATURE:
<223> OTHER INFORMATION: Oligonucleotide-11 is a 24-mer template
      oligonucleotide

<400> SEQUENCE: 11
tttattcatc gcgcaacagt gttt                                               24

<210> SEQ ID NO 12
<211> LENGTH: 13
<212> TYPE: DNA
<213> ORGANISM: Artificial Sequence
<220> FEATURE:
<223> OTHER INFORMATION: 5'-RES2334 with a 2'-azidoethoxy-T monomer
      incorporated into oligonucleotide internally after nucleotide
      number 6

<400> SEQUENCE: 12
acagaatcat att                                                           13

<210> SEQ ID NO 13
<211> LENGTH: 13
<212> TYPE: DNA
<213> ORGANISM: Artificial Sequence
<220> FEATURE:
<223> OTHER INFORMATION: 5'-RES2333 with 5-propargyl DIBO d monomer for
      labelling oligonucleotides internally and incorporated internally
      after nucleotide number 8

<400> SEQUENCE: 13
aatatgaatc tgt                                                           13
```